(12) United States Patent
Cole et al.

(10) Patent No.: US 10,493,201 B2
(45) Date of Patent: Dec. 3, 2019

(54) CANNULA INSERTION AND RETRACTION DEVICE FOR INFUSION DEVICE

(71) Applicant: Becton, Dickinson and Company, Franklin Lakes, NJ (US)

(72) Inventors: Russell Cole, River Vale, NJ (US); Michael Creighton, Hatboro, PA (US); Shuichi Amano, Bethlehem, PA (US); Gary Reuther, Warminster, PA (US); Arthur Klotz, Willow Grove, PA (US); Alyssa Jackson, Philadelphia, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 291 days.

(21) Appl. No.: 15/301,320

(22) PCT Filed: Apr. 23, 2015

(86) PCT No.: PCT/US2015/027360
§ 371 (c)(1),
(2) Date: Sep. 30, 2016

(87) PCT Pub. No.: WO2015/164647
PCT Pub. Date: Oct. 29, 2015

(65) Prior Publication Data
US 2017/0021096 A1 Jan. 26, 2017

Related U.S. Application Data

(60) Provisional application No. 61/983,985, filed on Apr. 24, 2014.

(51) Int. Cl.
*A61M 5/158* (2006.01)
*A61M 5/142* (2006.01)
*A61M 5/162* (2006.01)

(52) U.S. Cl.
CPC ........ *A61M 5/158* (2013.01); *A61M 5/14248* (2013.01); *A61M 5/162* (2013.01);
(Continued)

(58) Field of Classification Search
CPC .. A61M 5/158; A61M 5/162; A61M 5/14248; A61M 2005/1585; A61M 2005/14252; A61M 2005/1583
See application file for complete search history.

(56) References Cited

U.S. PATENT DOCUMENTS

2007/0293826 A1* 12/2007 Wall .................. A61M 5/19
604/200
2010/0286615 A1* 11/2010 Gyrn .................. A61M 5/158
604/164.04

(Continued)

FOREIGN PATENT DOCUMENTS

| JP | 2007-502169 A | 2/2007 |
| JP | 2010-531692 A | 9/2010 |

*Primary Examiner* — Bhisma Mehta
*Assistant Examiner* — Hamza A Darb
(74) *Attorney, Agent, or Firm* — Dickinson Wright, PLLC

(57) ABSTRACT

An insulin infusion device (1A) is disclosed. The device includes a body (3A), cannula (70) housed in the body (1A), a cannula insertion device (10, 20, 23) and a cannula retraction device (20, 23, 30). When the cannula insertion device is activated, the cannula (70) extends at least partly out of the body (1A) and into an infusion site and when the cannula retraction device is activated after the cannula insertion device has been activated, the cannula (70) retracts into the body (1A).

15 Claims, 35 Drawing Sheets

(52) U.S. Cl.
CPC .............. *A61M 2005/14252* (2013.01); *A61M 2005/1585* (2013.01)

(56) References Cited

U.S. PATENT DOCUMENTS

| | | |
|---|---|---|
| 2011/0054285 A1 | 3/2011 | Searle et al. |
| 2011/0054390 A1* | 3/2011 | Searle ................. A61M 5/1413 604/66 |
| 2011/0313357 A1* | 12/2011 | Skutnik ............. A61M 5/14248 604/151 |
| 2012/0316506 A1 | 12/2012 | Sonderegger et al. |
| 2013/0066274 A1 | 3/2013 | O'Connor et al. |
| 2013/0204191 A1* | 8/2013 | Cindrich ........... A61M 5/14248 604/180 |

\* cited by examiner

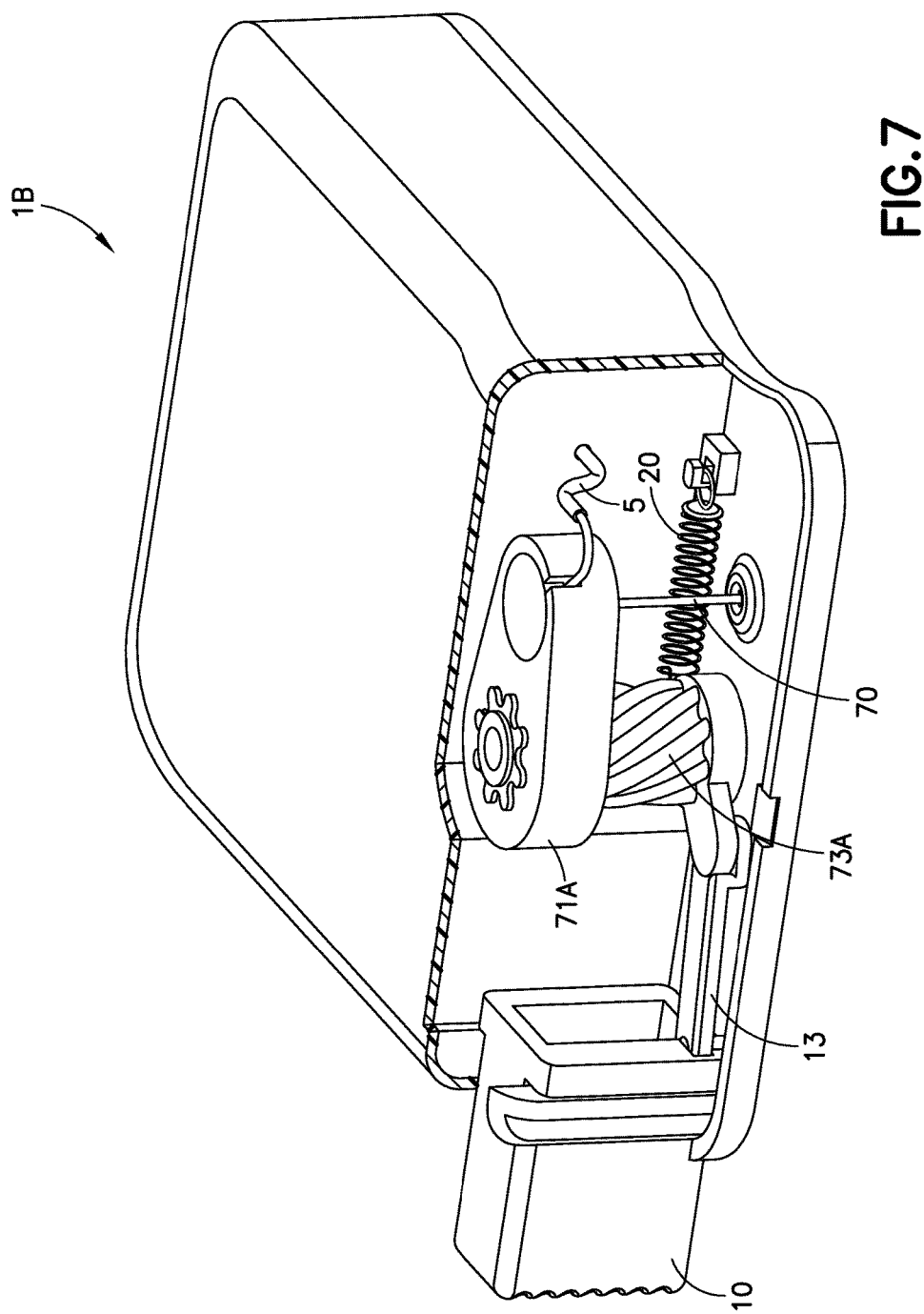

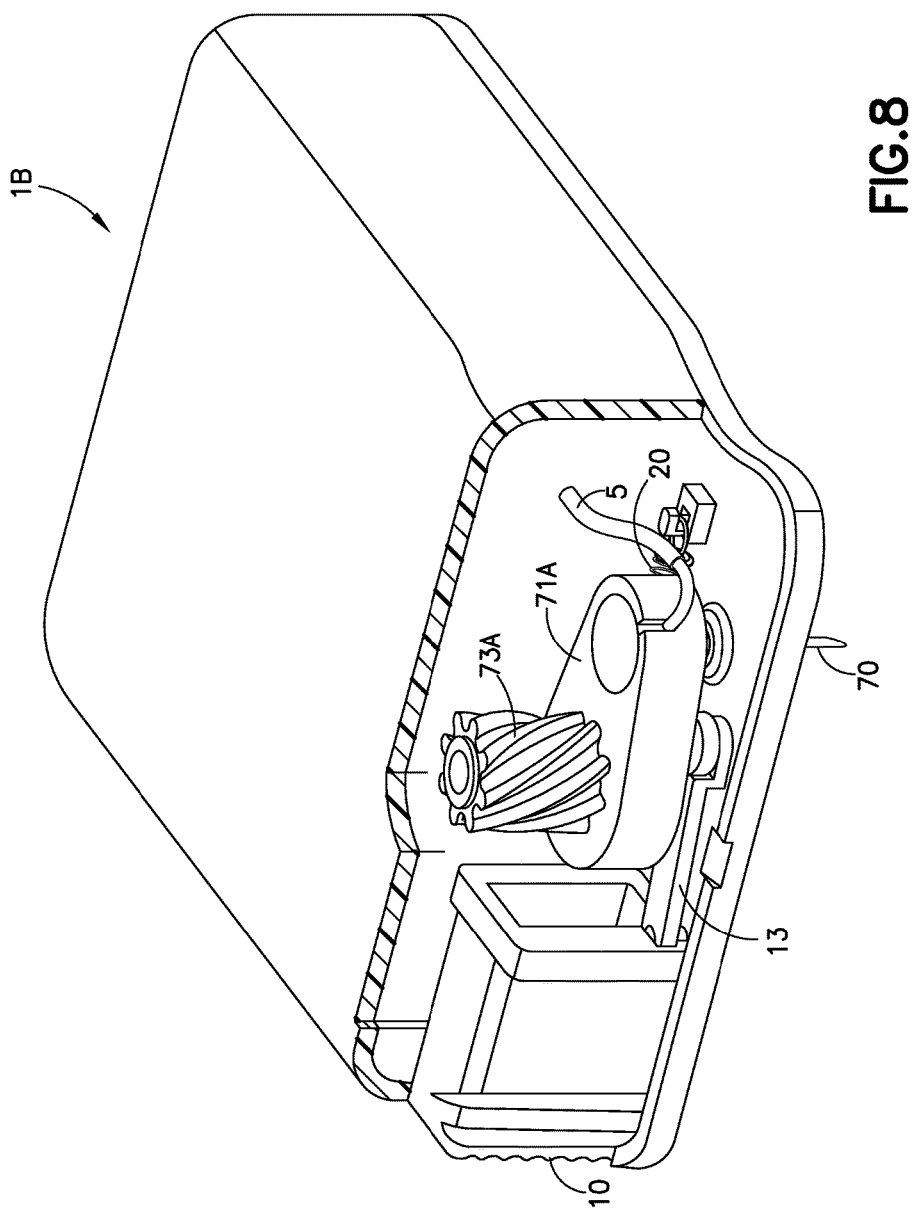

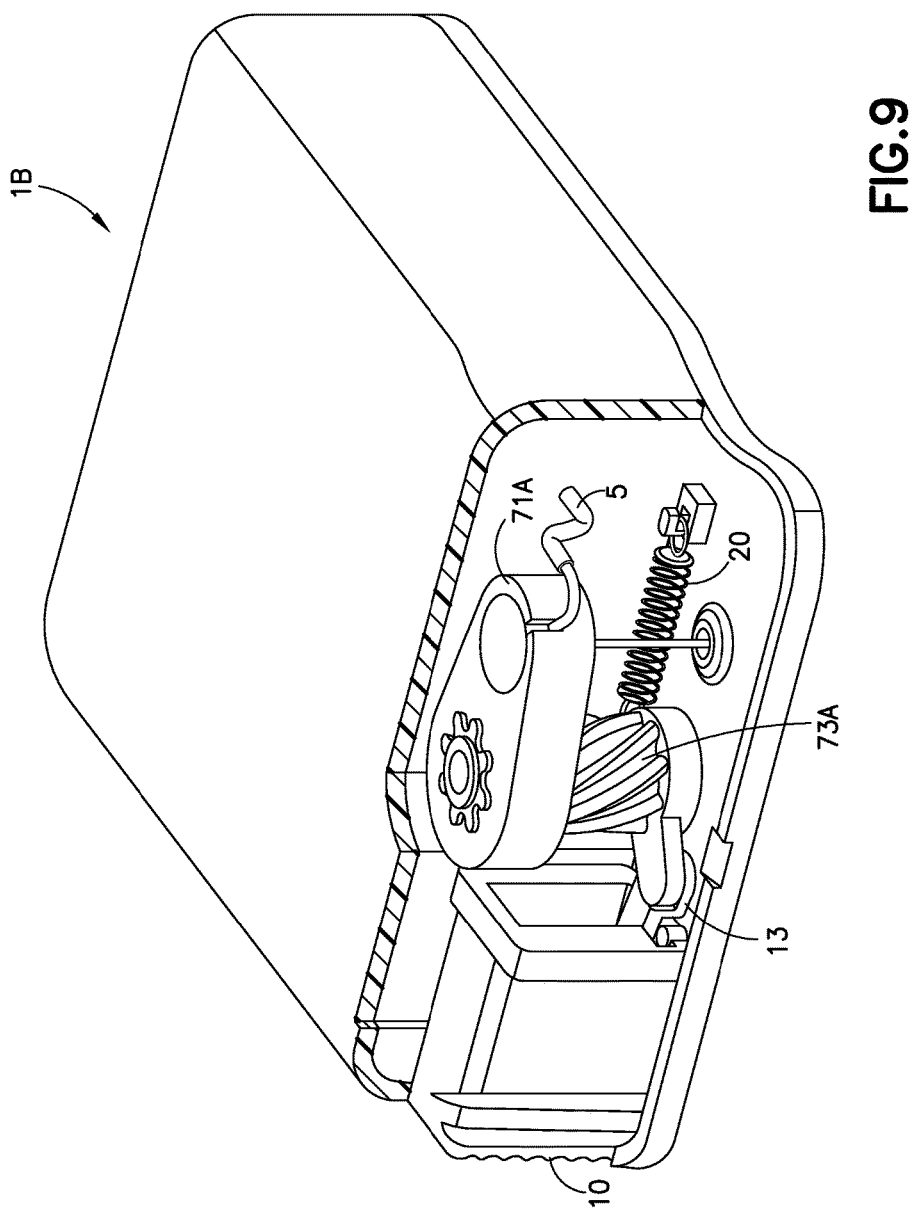

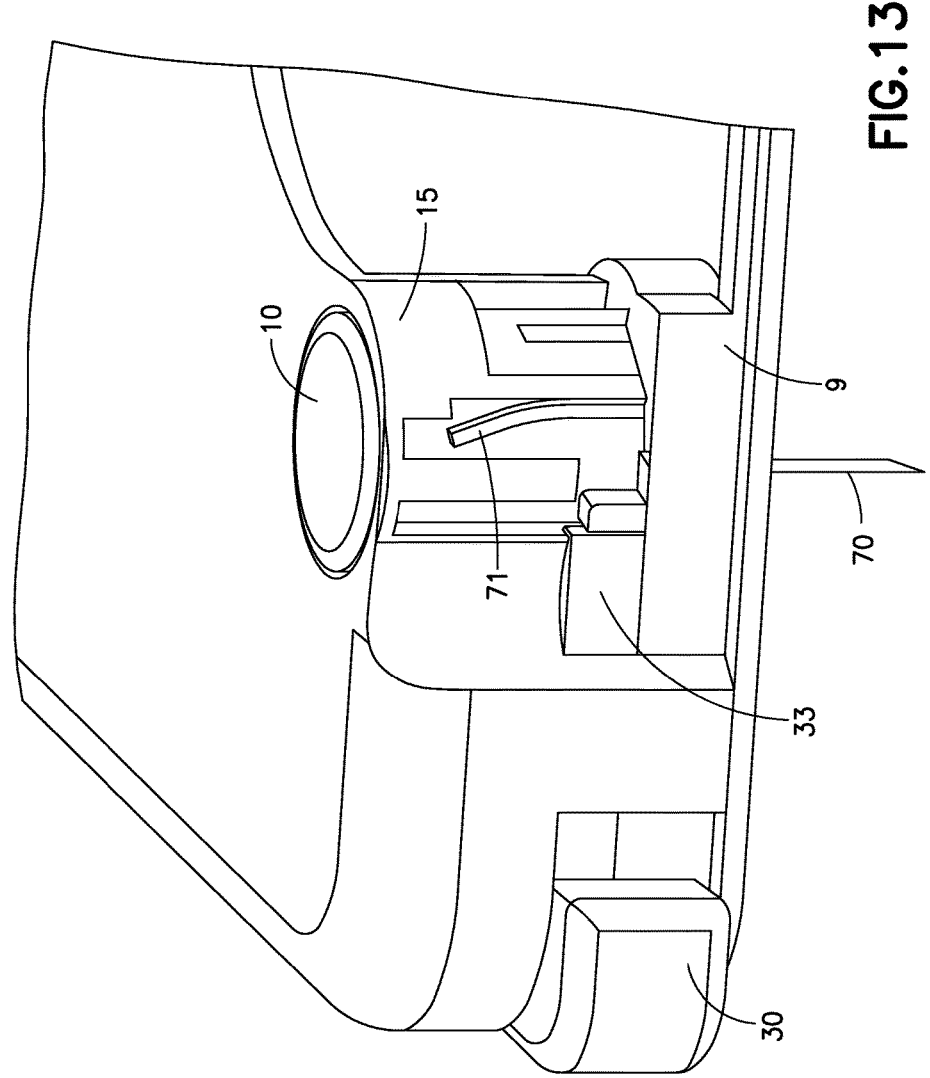

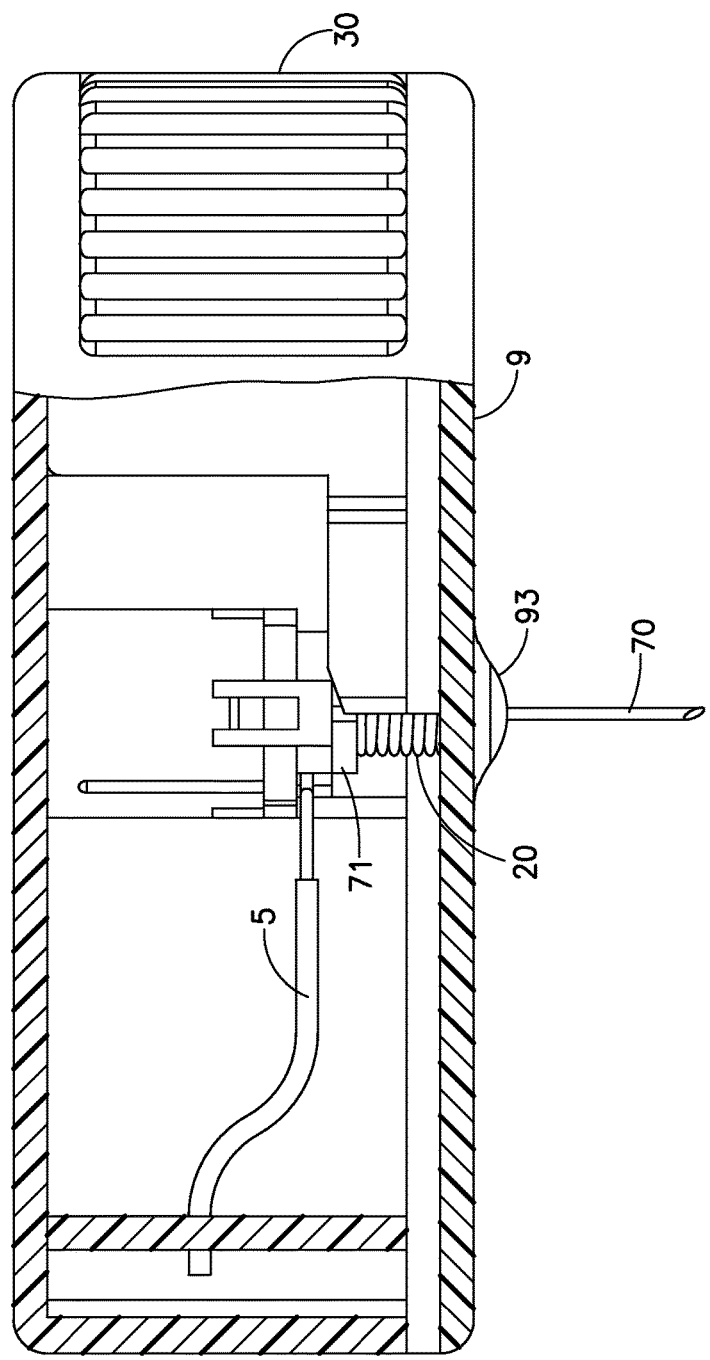

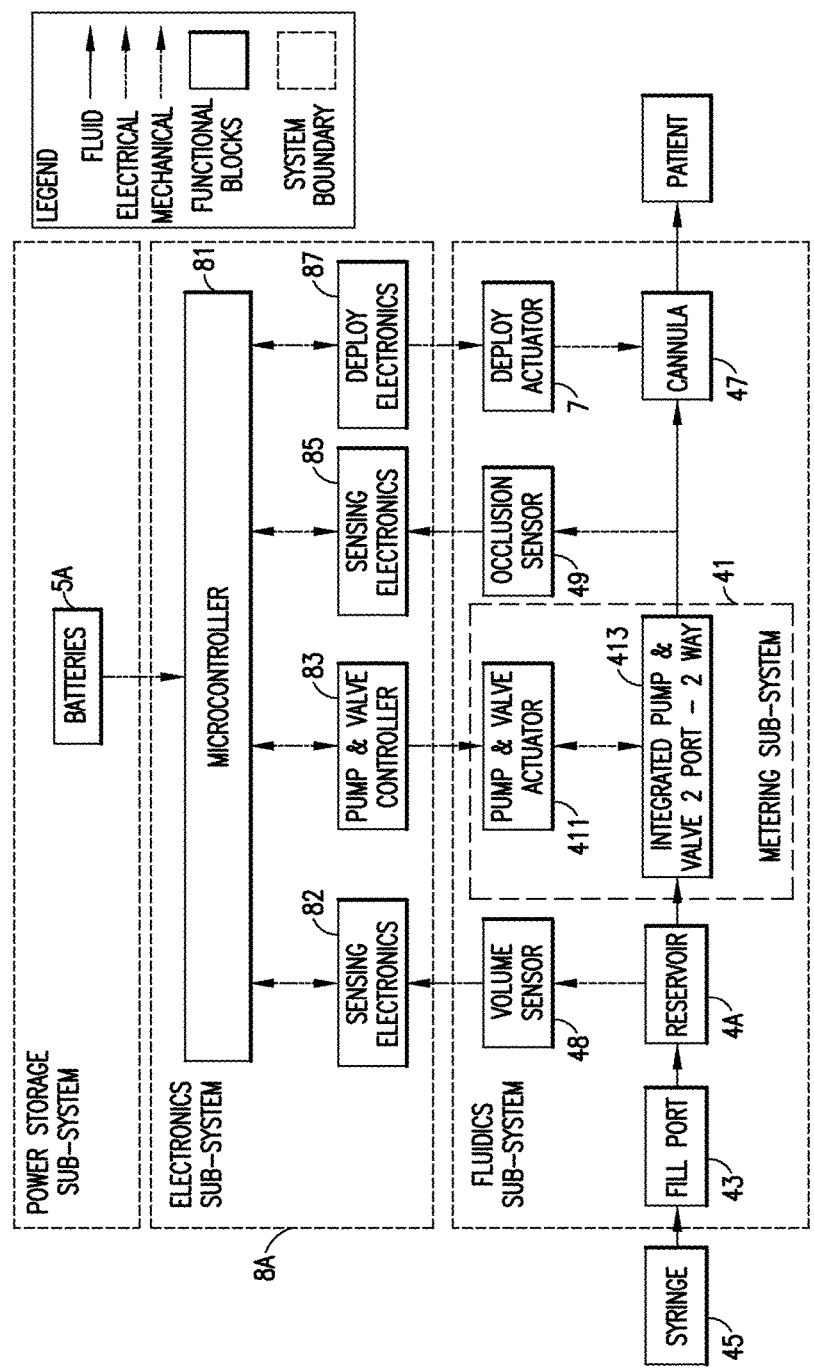

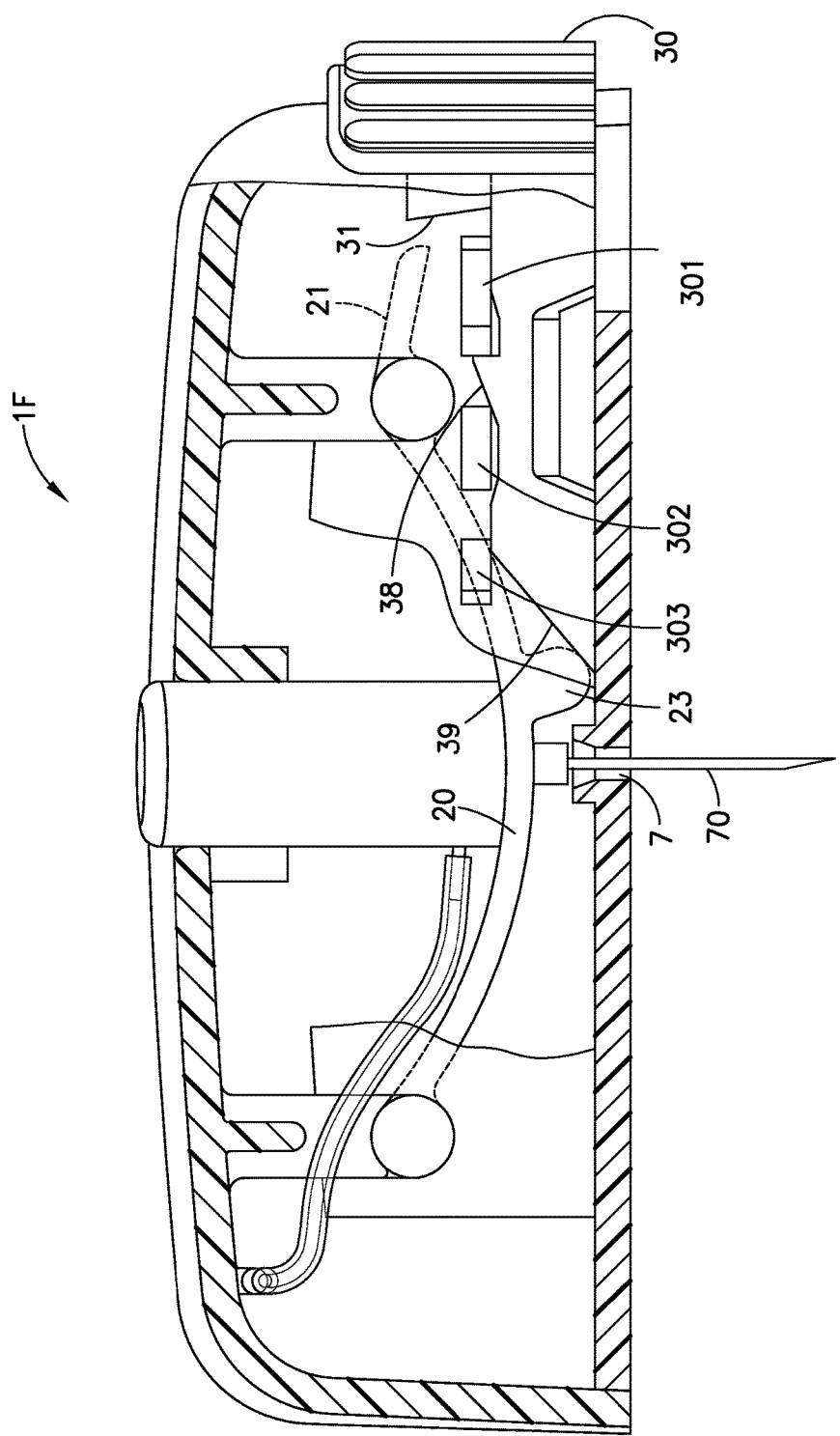

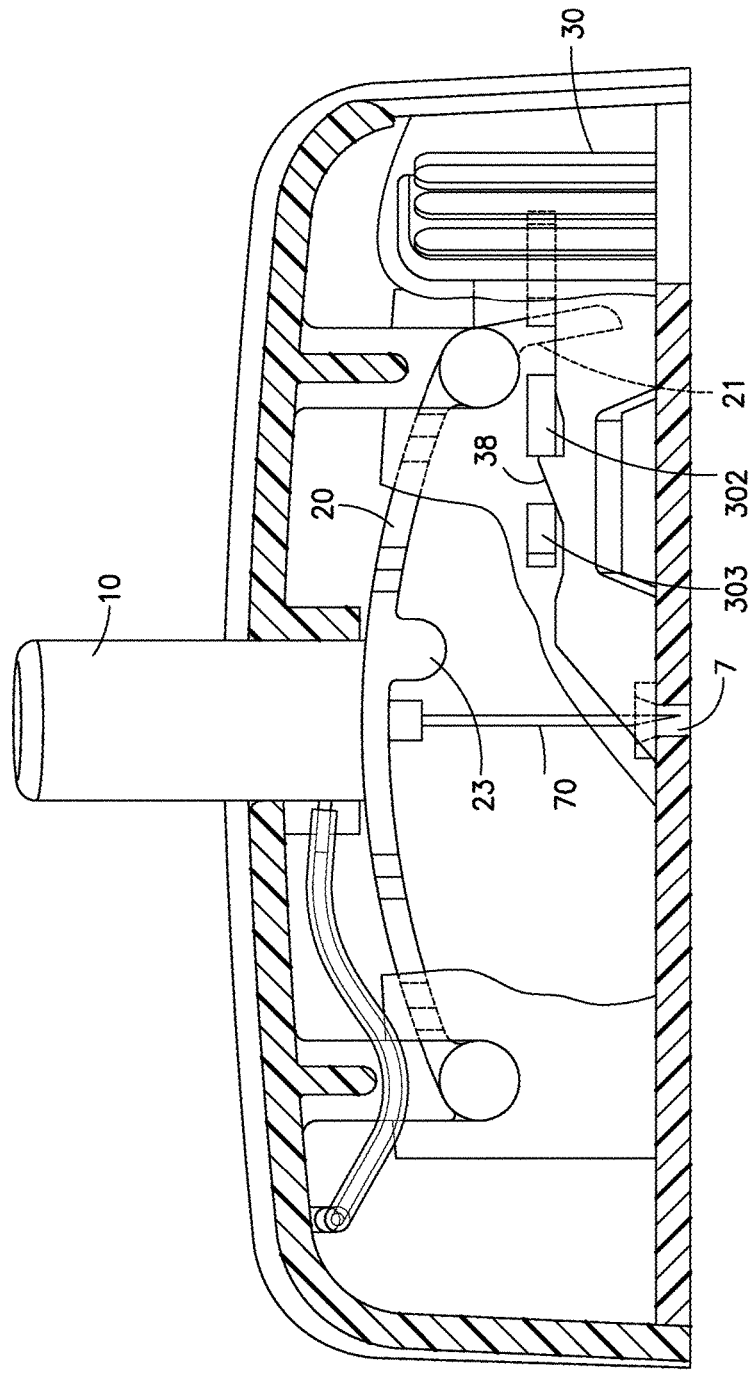

CANNULA INSERTION AND RETRACTION DEVICE FOR INFUSION DEVICE

CROSS-REFERENCE TO RELATED APPLICATION

This application claims the benefit under 35 U.S.C. § 119(e) of U.S. Provisional Application No. 61/983,985, filed on Apr. 24, 2014 in the U.S. Patent and Trademark Office, the disclosure of said application being incorporated herein by reference in its entirety.

FIELD OF THE INVENTION

The present invention relates generally to medical infusion systems, such as an insulin infusion device, where a cannula is inserted into an infusion site of a user for delivery of liquid medication via the cannula.

BACKGROUND OF THE INVENTION

A large number of people suffering from diabetes use some form of daily insulin therapy to maintain close control of their glucose levels. Currently, there are two principal modes of daily insulin therapy. The first mode includes syringes and insulin pens. These devices are simple to use and are relatively low in cost, but they require a needle stick at each injection, typically three to four times per day. The second mode includes infusion pump therapy, which entails the purchase of an insulin pump that lasts for about three years. The initial cost of the pump can be significant, but is superior from a user perspective. Consequently, the overwhelming majority of patients who have used pumps prefer to remain with pumps.

Infusion pumps, although more complex than syringes and pens, offer the advantages of continuous infusion of insulin, precision dosing and programmable delivery schedules. This results in closer blood glucose control and an improved feeling of wellness.

The use of an infusion pump requires the provision of a number of components including disposable components, such as an infusion set or pump set, which conveys the insulin from a reservoir within the pump into the skin of the user. An infusion set typically consists of a pump connector, a length of tubing, and a hub or base from which an infusion cannula or catheter extends. The hub or base has an adhesive that retains the base on the skin surface during use. Once applied, the infusion cannula or catheter can be inserted into the skin with the aid of a manual or automatic insertion device.

Another type of insulin pump is a patch pump. Unlike a conventional infusion pump and infusion set combination, a patch pump is an integrated device that combines most or all of the fluidic components, including the fluid reservoir, pumping mechanism and mechanism for automatically inserting the cannula, in a single housing which is adhesively attached to an infusion site on the patient's skin, and does not require the use of a separate infusion or tubing set. A patch pump containing insulin adheres to the skin and delivers the insulin over a period of time via an integrated subcutaneous cannula. Some patch pumps may wirelessly communicate with a separate controller device (as in one device sold by Insulet Corporation under the brand name OmniPod®), while others are completely self-contained. Such devices are replaced on a frequent basis, such as every three days, when the insulin reservoir is exhausted or complications may otherwise occur, such as restriction in the cannula or the infusion site.

There are many available types of infusion sets, including steel needle infusion sets and soft catheter sets. Steel needle infusion sets can be provided with a sharpened cannula which can be automatically or manually inserted into a patient and left in place with the set. Soft catheter sets are typically inserted into a patient with the aid of a manual or automatic insertion device using a steel introducer needle, which is removed from the patient after insertion to leave the soft catheter in place.

Infusion sets and patch pumps can be placed and manually or automatically activated to insert the cannula. In the case of manual activation, the insertion and retraction of the cannula can vary in response to the user force applied, and speed, smoothness and angle thereof. This variability can lead to an increased rate of insertion failure and/or discomfort to the user. Also, in each case, a large number of activation and retraction components may be required for the construction and use of the infusion set or patch pump. This leads to increased cost and a greater chance of failure or improper operation. Further, any requirement for a large number of components can result in a larger and heavier device, which is undesirable since it will add to the discomfort of the user.

Accordingly, a need exists for an infusion device that facilitates insertion of a cannula, and if required, retraction of the cannula, while reducing the number of components required for the construction and use of the infusion device.

SUMMARY OF THE INVENTION

An object of the present invention is to substantially address the above and other concerns, and provide advanced, improved, and novel components and elements of an infusion device that facilitates insertion of a cannula, and if required, retraction of the cannula, while reducing the number of components required for the construction and use of the infusion device.

Another object of the present invention is to provide an infusion device that can utilize components with one or more shared technical features such that each component can serve multiple functions.

Another object of the present invention is to provide an infusion device that can utilize components which serve multiple functions, such that the part count of the exemplary embodiments is lowered and which serves to keep part production costs low and simplify device assembly.

These and other objects are substantially achieved by providing an infusion device that includes a body, cannula housed in the body, a cannula insertion device, and a cannula retraction device, such that when the cannula insertion device is activated, the cannula extends at least partly out of the body and into an infusion site, and when the cannula retraction device is activated after the cannula insertion device has been activated, the cannula retracts into the body.

BRIEF DESCRIPTION OF THE DRAWINGS

The various objects, advantages and novel features of the exemplary embodiments of the present invention will be more readily appreciated from the following detailed description when read in conjunction with the appended drawings, in which:

FIG. 7 is a partial cross-sectional view of the exemplary infusion device of FIG. 6A before activation in accordance with an embodiment of the present invention;

FIG. 8 is a partial cross-sectional view of the exemplary infusion device of FIG. 6A at the beginning of activation in accordance with an embodiment of the present invention;

FIG. 9 is a partial cross-sectional view of the exemplary infusion device of FIG. 10A at the completion of activation in accordance with an embodiment of the present invention;

FIG. 13 is an enlarged partial cross-sectional view of the exemplary infusion device of FIG. 10A at the beginning of activation in accordance with an embodiment of the present invention;

FIG. 18 is a cross-sectional view of the exemplary infusion device of FIG. 16A at the beginning of activation in accordance with an embodiment of the present invention;

FIG. 31 is a patch-pump fluidic architecture and metering sub-system diagram of the patch pump of FIG. 30;

FIG. 34 is an enlarged cross-sectional view of the exemplary infusion device of FIG. 32A at the beginning of activation in accordance with an embodiment of the present invention; and FIG. 35 is an enlarged cross-sectional view of the exemplary infusion device of FIG. 32A at the completion of activation in accordance with an embodiment of the present invention.

Throughout the drawings, like reference numerals will be understood to refer to like parts, components and structures.

DETAILED DESCRIPTION OF THE EXEMPLARY EMBODIMENTS

The exemplary embodiments of the present invention described below provide novel means of providing one or more infusion device elements that are configured to share functions, thereby reducing the overall number of components required for the construction and use of the infusion device.

FIGS. 1A-5 illustrate an embodiment of the invention in the form of an infusion device with a bi-stable cannula insertion and retraction device or mechanism. The device 1A is used to insert a cannula 70, in the form of a hollow hypodermic needle, into an infusion site, typically the skin of a patient, deliver infusate, such as insulin, via the cannula 70, as well as retract the cannula 70 from infusion site. The actuation for the mechanism derives from pushing downwardly on an activation button 10 by the user. The activation button 10 is bi-stable in nature, meaning that it will stay at rest in two different orientations, one inserting the cannula 70 into the infusion site and another for retracting the cannula 70 from the infusion site, but not in between the two orientations. This bi-stable behavior allows the activation button 10 and cannula 70 to snap between the desired positions. A retraction button 30 is used to force the activation button 10 to retract the cannula 70 from the infusion site.

Pressing the activation button 10 causes a bi-stable band 20, made of an elastic material (such as plastic or metal) that could be a spring, to snap the cannula 70 downwardly out of the device 1A and into the infusion site. Pressing the separate retraction button 30 causes the activation button 10 to snap upward, retracting the cannula 70 from the infusion site.

Figure 1A:
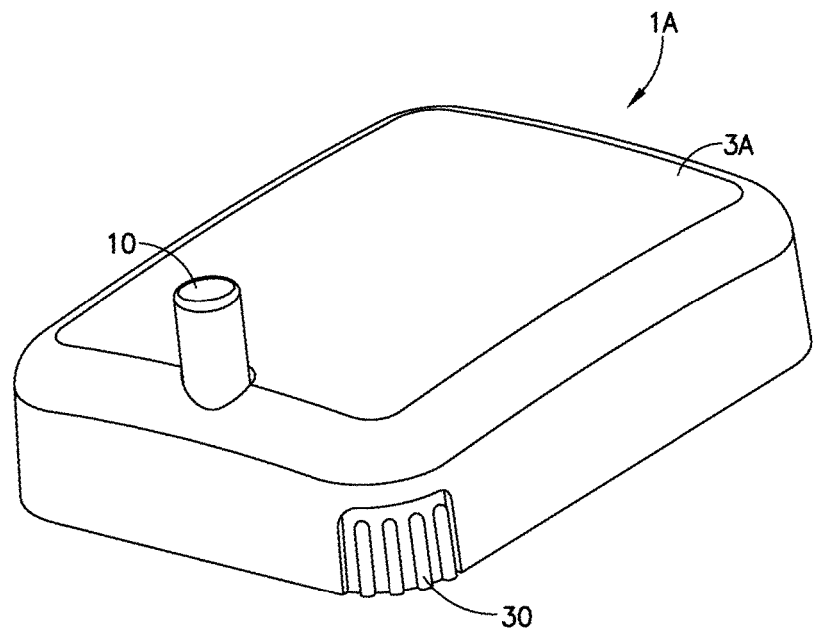
FIG. 1A is a perspective view of an exemplary infusion device prior to activation in accordance with an embodiment of the present invention.
Figure 1B:
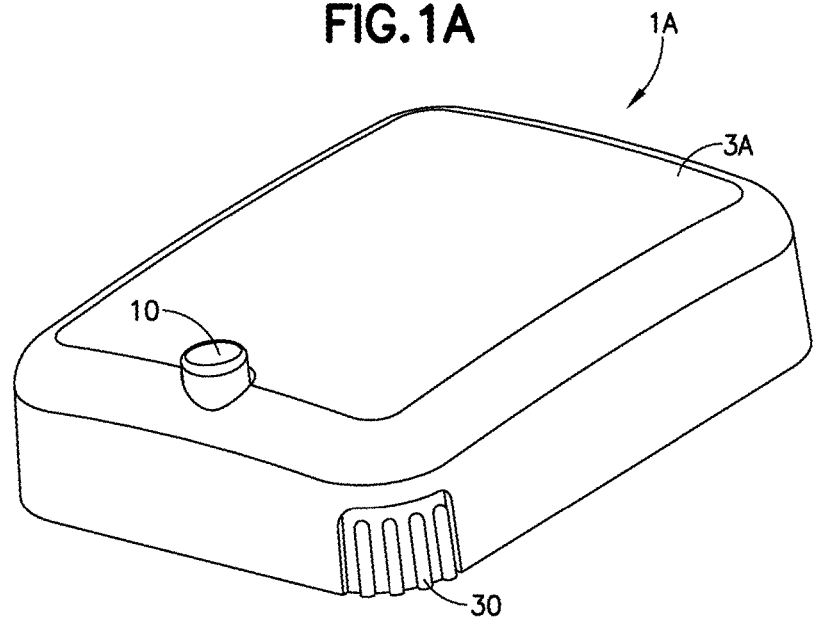
FIG. 1B is a perspective view of the exemplary infusion device of FIG. 1A after activation in accordance with an embodiment of the present invention.

FIG. 1A illustrates an exemplary infusion device 1A, prior to activation or in a pre-activation state and FIG. 1B is illustrates the exemplary infusion device 1A of FIG. 1A, after activation or in a post-activation state in accordance with an embodiment of the present invention. The device 1A is activated by pressing downward on the activation button 10, which protrudes from the top of the outer cover 3 of the device 1A.

Figure 2:
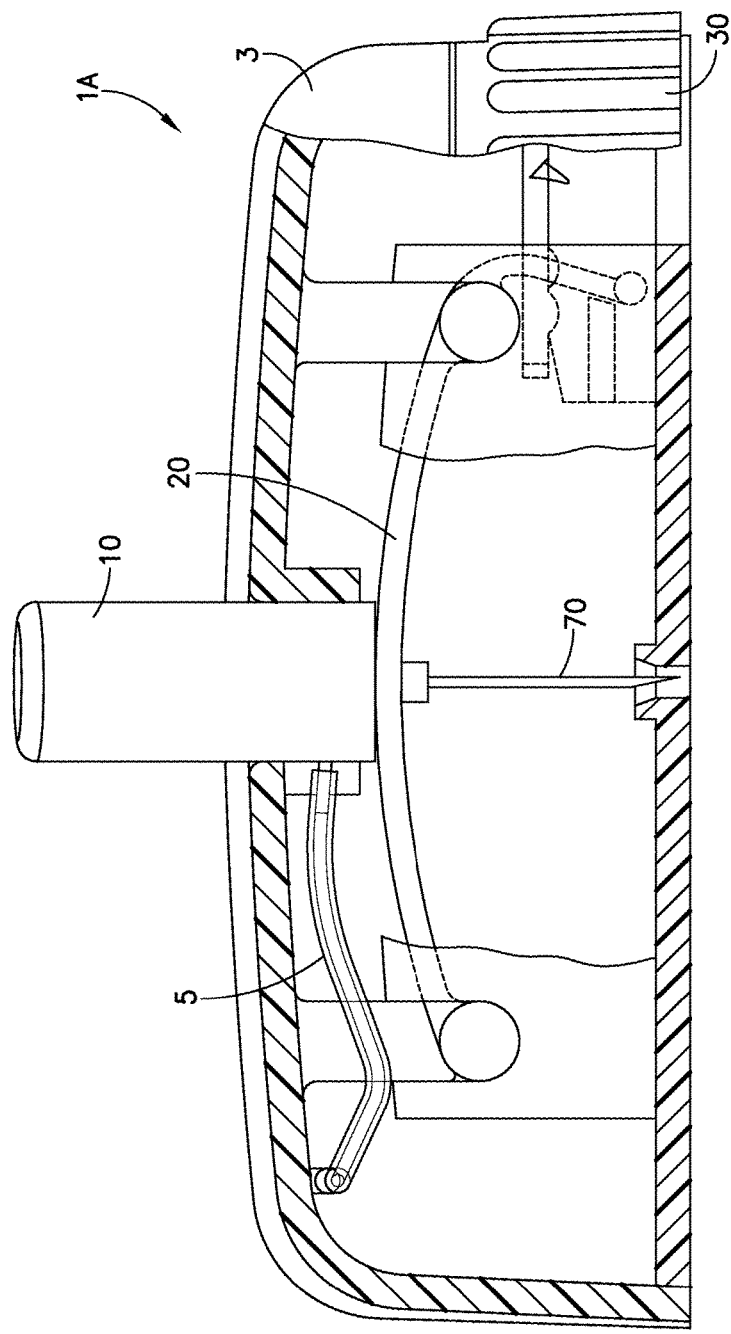
FIG. 2 is an enlarged cross-sectional view of the exemplary infusion device of FIG. 1A before activation in accordance with an embodiment of the present invention.

FIG. 2 is an enlarged cross-sectional view of the exemplary infusion device 1A of FIG. 1A before activation in accordance with an embodiment of the present invention. The cannula 70 is attached to the activation button 10 and connects to a flexible tubing 5 which is in fluid communication with an end of the cannula 70 to permit infusate to flow from a reservoir (not shown) to exit the open end of the cannula 70 via the flexible tubing 5. Such fluid connection exists similarly in the other embodiments of the specification.

The band 20, which can be part of the activation button 10, is arced upward (one of the two bi-stable positions) which holds the tip of the cannula 70 inside the device 1A. The nature of the bi-stable band 20 on the activation button requires a certain amount of downward force to be applied to the button before it will automatically snap to the inserted position (the second of the two bi-stable positions), as illustrated in FIG. 3.

Figure 3:
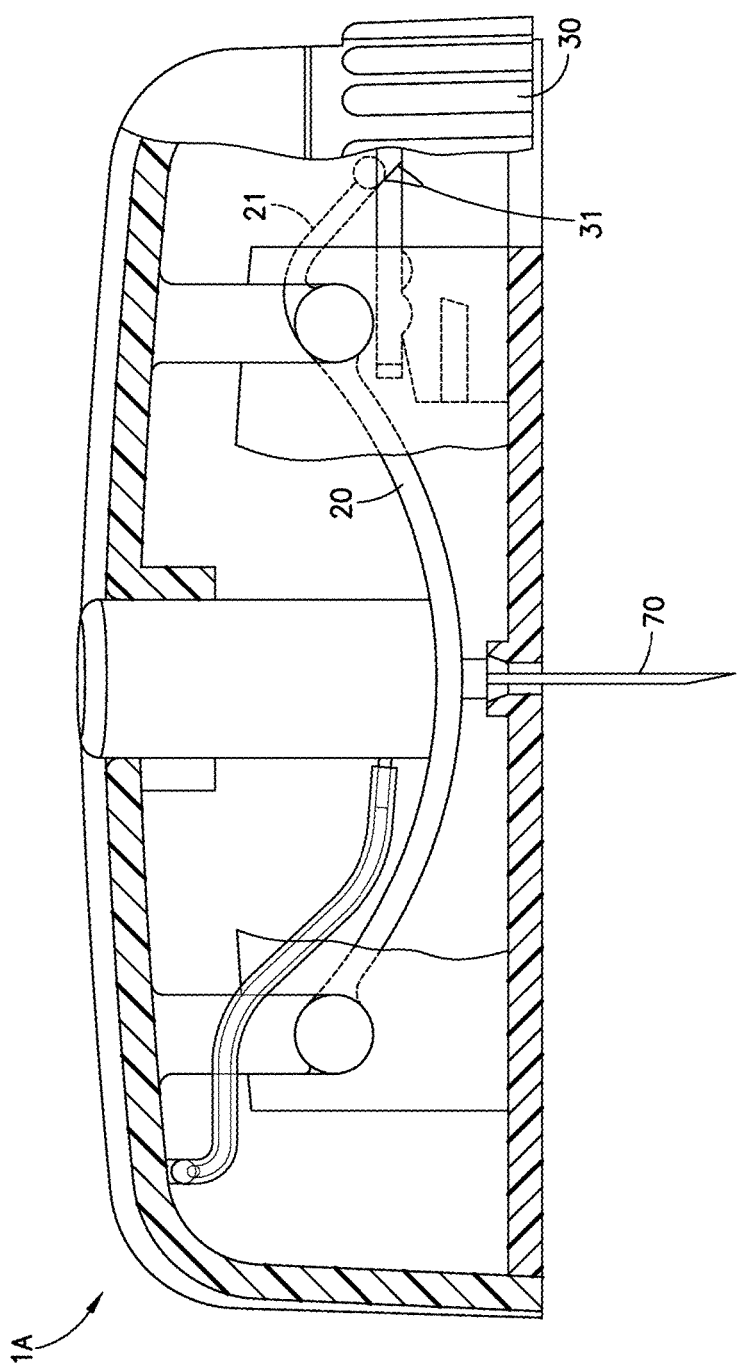
FIG. 3 is an enlarged cross-sectional view of the exemplary infusion device of FIG. 1A at the beginning of activation in accordance with an embodiment of the present invention.

FIG. 3 is an enlarged cross-sectional view of the exemplary infusion device 1A at the beginning of activation in accordance with an embodiment of the present invention. FIG. 3 illustrates the device once the activation button 10 has been pressed downwardly with enough force by the user to cause the band 20 to snap to the inserted position for extending the cannula 70 out of the device 1A. A small arm 21 on one end of the bi-stable band 20 flexes over a ramp 31 on the retraction button 30, to ensure that the band 20 cannot snap upward accidentally or unintentionally. The device will remain in this position for the full duration of infusion therapy, typically up to three days. The combination of elements above, including the activation button 10, bi-stable band 20 and small arm 21 can be described as a cannula insertion device.

Figure 4:
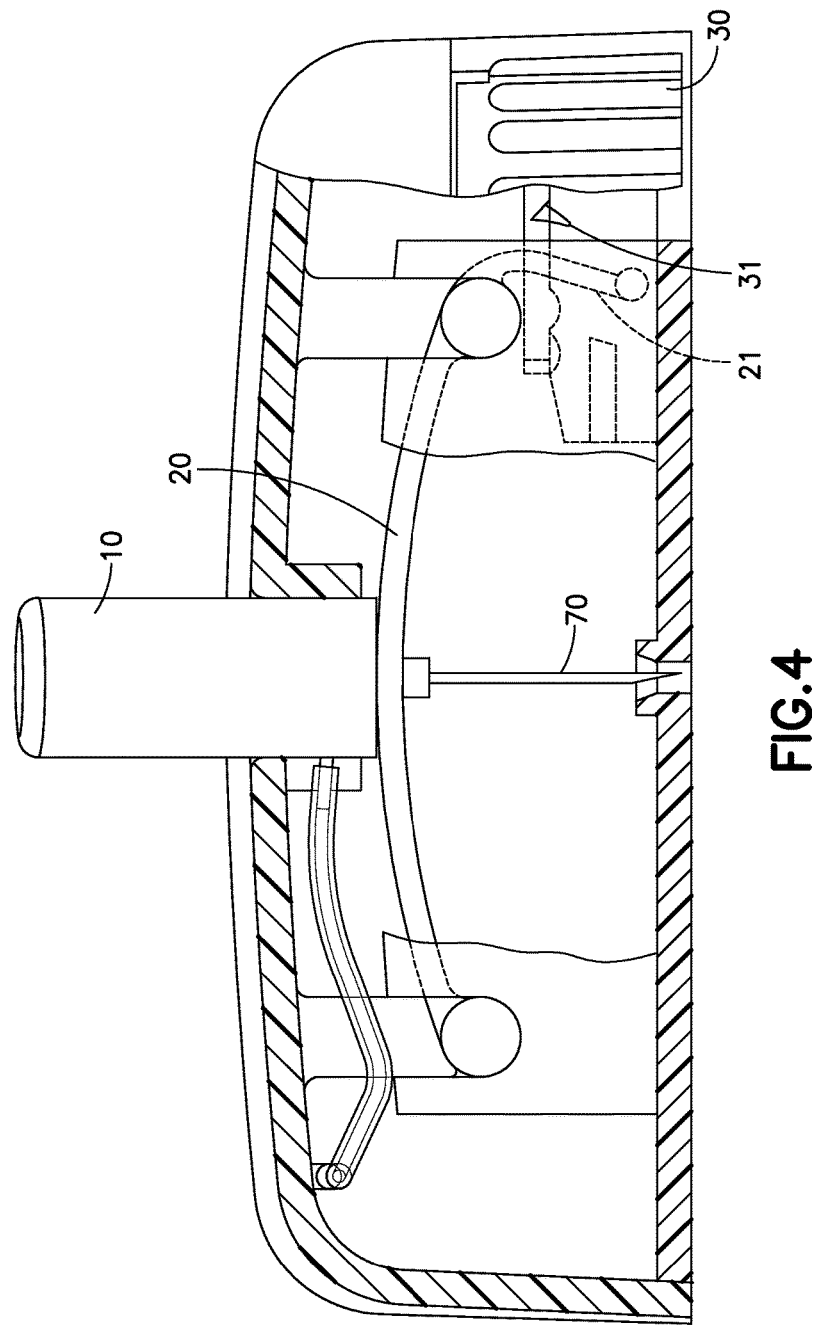
FIG. 4 is an enlarged cross-sectional view of the exemplary infusion device of FIG. 1A at the completion of activation in accordance with an embodiment of the present invention.

FIG. 4 is an enlarged cross-sectional view of the exemplary infusion device 1A at the completion of activation in accordance with an embodiment of the present invention. To retract the cannula 70, the retraction button 30 is pressed inwardly in relation to the device 1A by the user. This forces the small arm 21 on the bi-stable band 20 to flex inward, which then causes the band 20 to snap upward, retracting the cannula 70 into the device 1A. A feature (not shown) may be configured to prevent the activation button 10 from being pressed again, to prevent the device 1A from being used a second time. The combination of elements above, including the retraction button 30, bi-stable band 20 and small arm 21 can be described as a cannula retraction device.

The bi-stable nature of the activation button 10 simplifies the insertion mechanism 1A by eliminating and combining some of the parts that are traditionally used to insert and retract a cannula. This embodiment only requires two parts, the activation button and the retraction button to enable the activation and retraction of the cannula 70.

Figure 5:
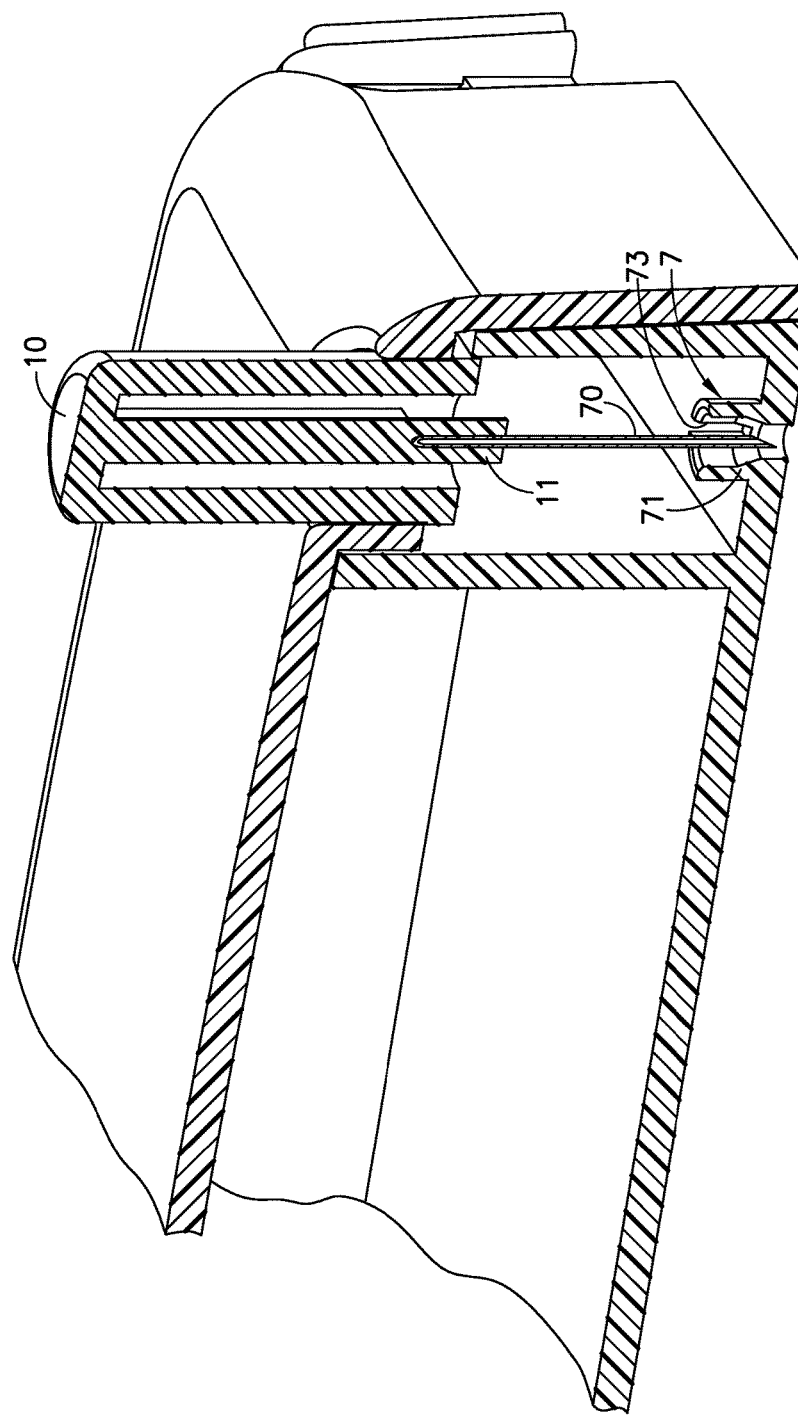
FIG. 5 is an enlarged perspective view of an exemplary cannula exit of the exemplary infusion device of FIG. 1A in accordance with an embodiment of the present invention.

FIG. 5 is an enlarged perspective view of a modification of the cannula exit 7 of the infusion device 1A in accordance with an embodiment of the present invention. The cannula exit 7 could comprise a barrel 71 that extends into the housing of the device 1A. A slot 73 on the side of the barrel 71 could allow the cannula 70 to be assembled into the barrel 71 from the side which may reduce the risk of tip damage to the cannula 70. Once assembled from the side the cannula 70 can be inserted farther into the barrel 71 to the pre-activation position, guided by the inner walls of the barrel 71. The barrel 71 would be able support the cannula 70 during insertion, preventing any buckling that may occur from any tilting caused by the compliance or tolerances of the activation button 70 and/or in the event of an off axis of the cannula 70. The cannula glue well portion 11 of the activation button 10 cab travel into the barrel 71 toward the insertion end of the cannula 70.

FIGS. 6-9 illustrate another embodiment of the invention in the form of an infusion device with a helical insertion and retraction mechanism. Pressing inwardly on the activation button 10 causes a helical post 73A to rotate which forces the cannula 70 downward. By pressing a separate retraction button 30, the helical post 73A rotates in the opposite direction and the cannula 70 is retracted from the infusion site.

The actuation for this device 1B occurs when a user pushes on the activation button 10. This inward motion causes a helical post 71, in connection with the activation button 10, to rotate, which drives the cannula 70 downward. A retraction button 30 is used, when activated, to turn the helical post in the opposite direction, which retracts the cannula 70, which retracts activation button 10 inside the device 1B, as illustrated in FIG. 9.

Figure 6A:
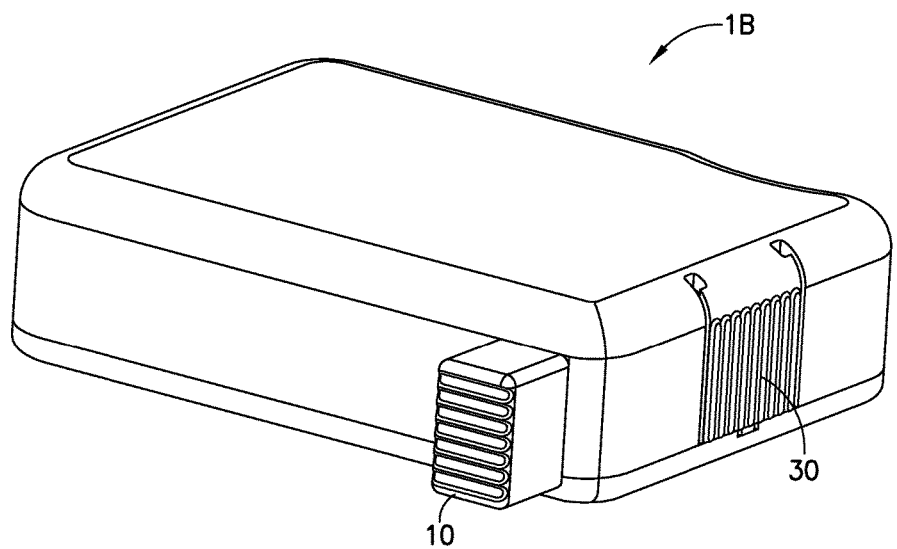
FIG. 6A is a perspective view of another exemplary infusion device prior to activation in accordance with an embodiment of the present invention.
Figure 6B:
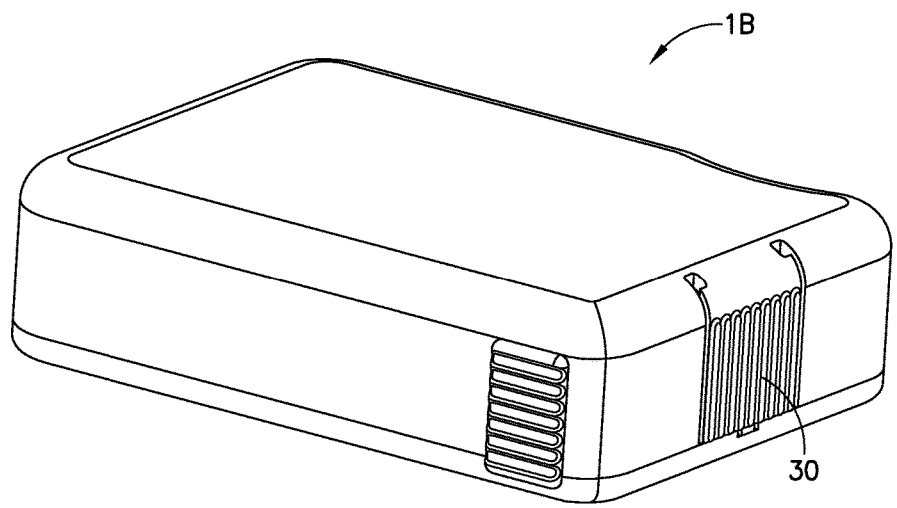
FIG. 6B is a perspective view of the exemplary infusion device of FIG. 6A after activation in accordance with an embodiment of the present invention.

FIG. 6A is a perspective view of the infusion device 1B prior to activation in accordance with an embodiment of the present invention. FIGS. 6A-6B illustrate the device 1B in the pre-activation (FIG. 6A) and post-activation (FIG. 6B) states. The device 1B is activated by pressing on the activation button 10, which protrudes from a side of the housing of the device 1B. The retraction button 30, on a front surface of the device can be molded as part of the outer cover to minimize interference with a user when the device 1B is attached to the user. FIG. 6B is a perspective view of the exemplary infusion device of FIG. 6A after activation in accordance with an embodiment of the present invention.

FIG. 7 is a partial cross-sectional view of the exemplary infusion device 1B of FIG. 6A before activation in accordance with an embodiment of the present invention. FIG. 7 illustrates a cutaway view of the device 1B with a portion of the outer cover removed for clarity. By pressing inwardly on the activation button 10, a linkage 13 that connects the activation button 10 and the helical post 73A, forces the helical post 73A to rotate and drive a cannula carrier 71A downward to insert the cannula 70 into the infusion site. During this process an extension spring 20 connected to the helical post 73 is compressed as the helical post 73A is rotated.

FIG. 8 is a partial cross-sectional view of the exemplary infusion device 1B of FIG. 6A at the beginning of activation in accordance with an embodiment of the present invention. FIG. 8 illustrates the device 1B once the activation button 10 has been fully pressed. The device 1B will remain in this state for the duration of infusate treatment. By pressing on the molded-on retraction button 30 on the front of the outer cover of the device 1B, the linkage 13 will be separated from the activation button 10 and the extension spring 20 will decompress to rotate the helical post 73A, causing the cannula 70 to be retracted into the device 1B, as the cannula carrier 71A is directed upward, as illustrated in FIG. 9.

FIG. 9 is a partial cross-sectional view of the exemplary infusion device 1B of FIG. 6A at the completion of activation in accordance with an embodiment of the present invention. FIG. 9 illustrates the device 1B with the cannula 70 fully retracted into the device 1B. As the spring 20 decompressed, the helical post 73A rotates, causing linkage 13 to be pushed inwardly into the activation button 10 while decoupling the linkage 13 from the activation button. FIG. 9 illustrates the linkage 13 resting inside the activation button 10. Since the activation button 10 does not return to its pre-activation position (as illustrated in FIG. 9), it is not possible to activate the device 1B a second time, by pushing on the activation button 10.

The combination of elements that can include activation button 10, linkage 13, helical post 73A, cannula carrier 71A can be described as a cannula insertion device. The combination of elements that can include retraction button 30, linkage 13, helical post 73A, cannula carrier 71A can be described as a cannula retraction device.

FIGS. 10-15 illustrate another embodiment of the invention in the form of an infusion device 1C with an off-center cannula insertion and retraction mechanism. Pressing downward on the activation button 10 drives a cannula guide 15 downward, compresses a spring 20, and inserts a hollow metal cannula 70 into the infusion site. By pressing a separate release or retraction button 30, the activation button 10 rotates and is no longer held down by the base 9 of the device 10, and the spring 20 decompresses, forcing the cannula carrier 71 and the activation button 10 upward and retracting the cannula 70 from the infusion site and into the device 10.

The device 1C is used to insert a cannula 70 into an infusion site, as well as to retract the cannula 70 from the infusion site. The actuation for the device 10 occurs when a user pushes downwardly on the activation button 10. The activation button 10 then drives the cannula guide 15 downward, which inserts the cannula 70 into infusion site. At the same time, the cannula guide 15 also compresses the spring 20 that will later be used for retraction of the cannula 70. For retraction of the cannula 70, the release button 30 is pressed from a side of the device 1C in order to rotate the cylindrically-shaped activation button 10, which disengages it from the base 9 and allows the spring 20 to de-compress, forcing the activation button 10 and cannula guide 15 upward, retracting the cannula 70 from the infusion site and into the device 1C.

Figure 10A:
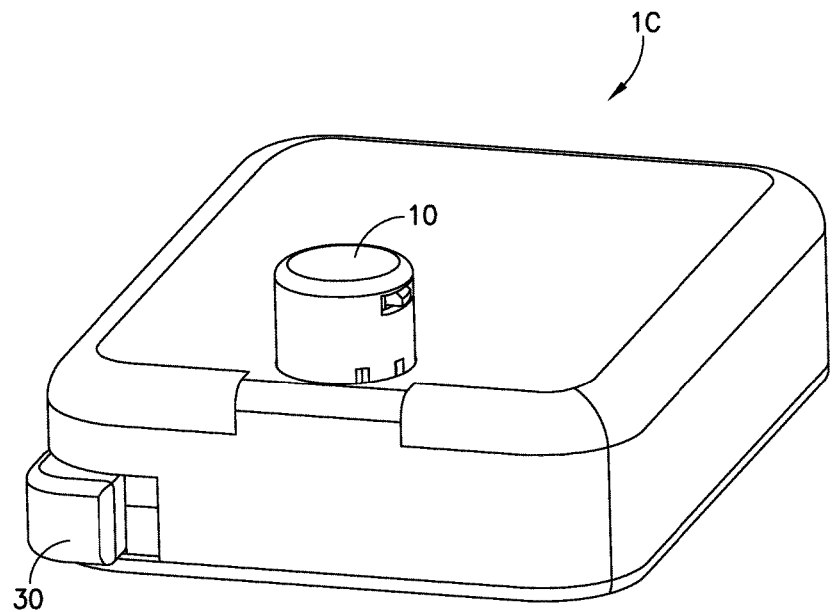
FIG. 10A is a perspective view of another exemplary infusion device prior to activation in accordance with an embodiment of the present invention.
Figure 10B:
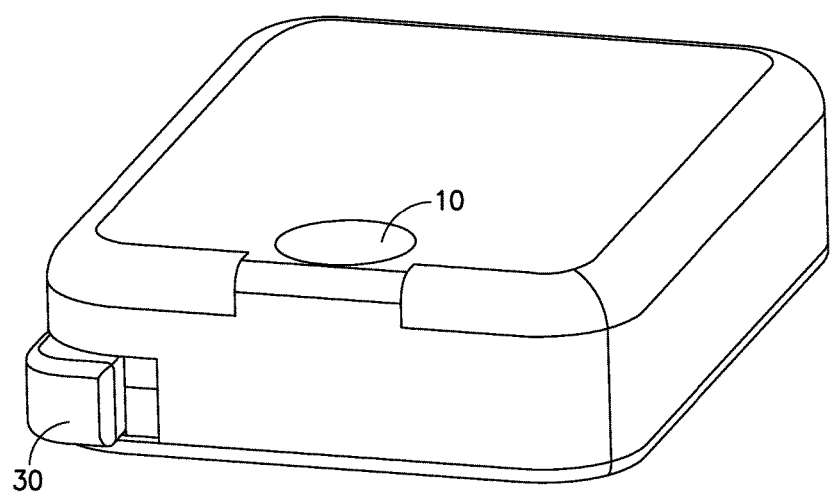
FIG. 10B is a perspective view of the exemplary infusion device of FIG. 6A after activation in accordance with an embodiment of the present invention.
Figure 11:
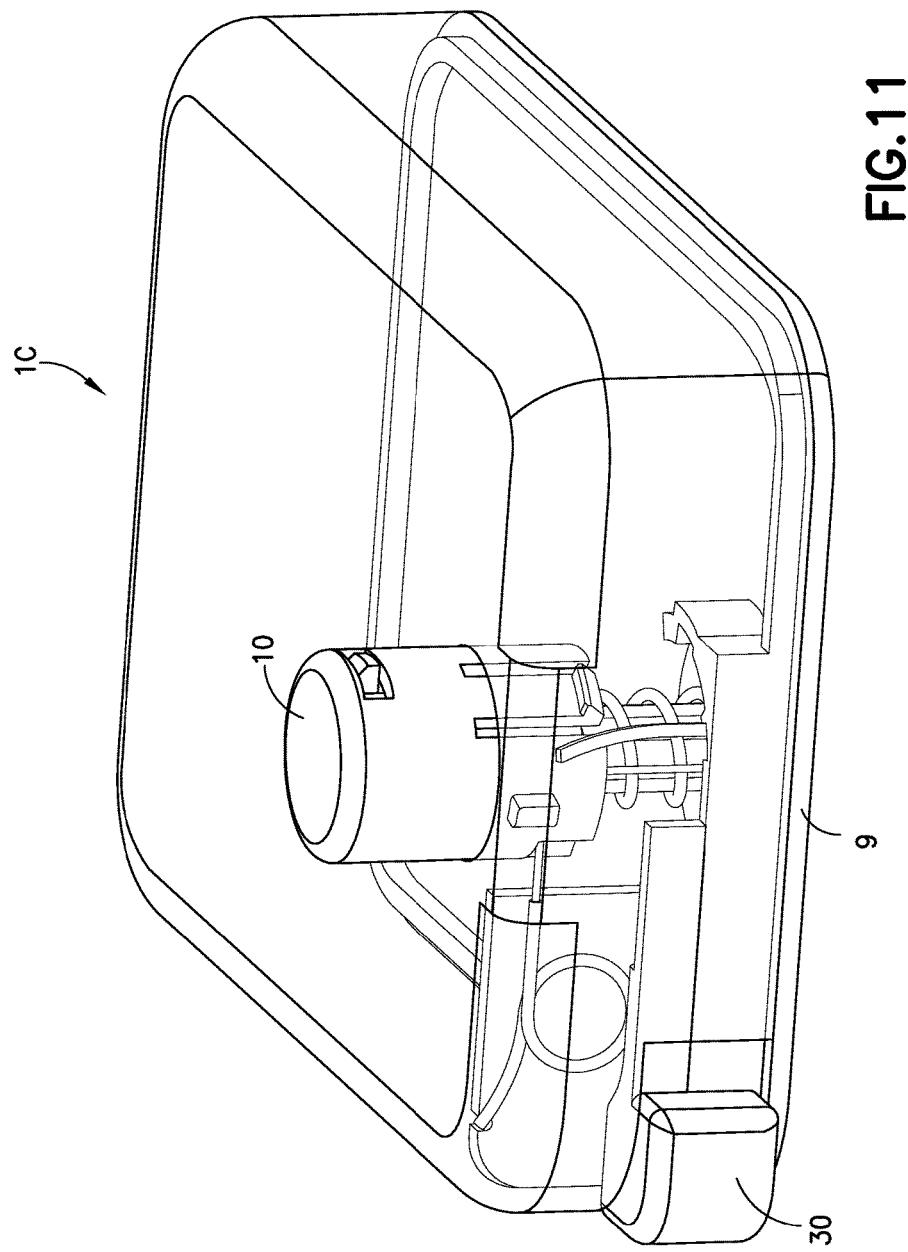
FIG. 11 is a perspective view of the exemplary infusion device of FIG. 10A, illustrated with a see-through cover.

FIGS. 10A and 10B illustrate the device in the pre-activation (FIG. 10A) and post-activation (FIG. 10B) states. The device 100 is activated by pressing downward on the activation button 10, which protrudes from the top of the housing of the device 10. FIG. 11 illustrates a perspective view of the device, illustrated with a see-through cover.

Figure 12:
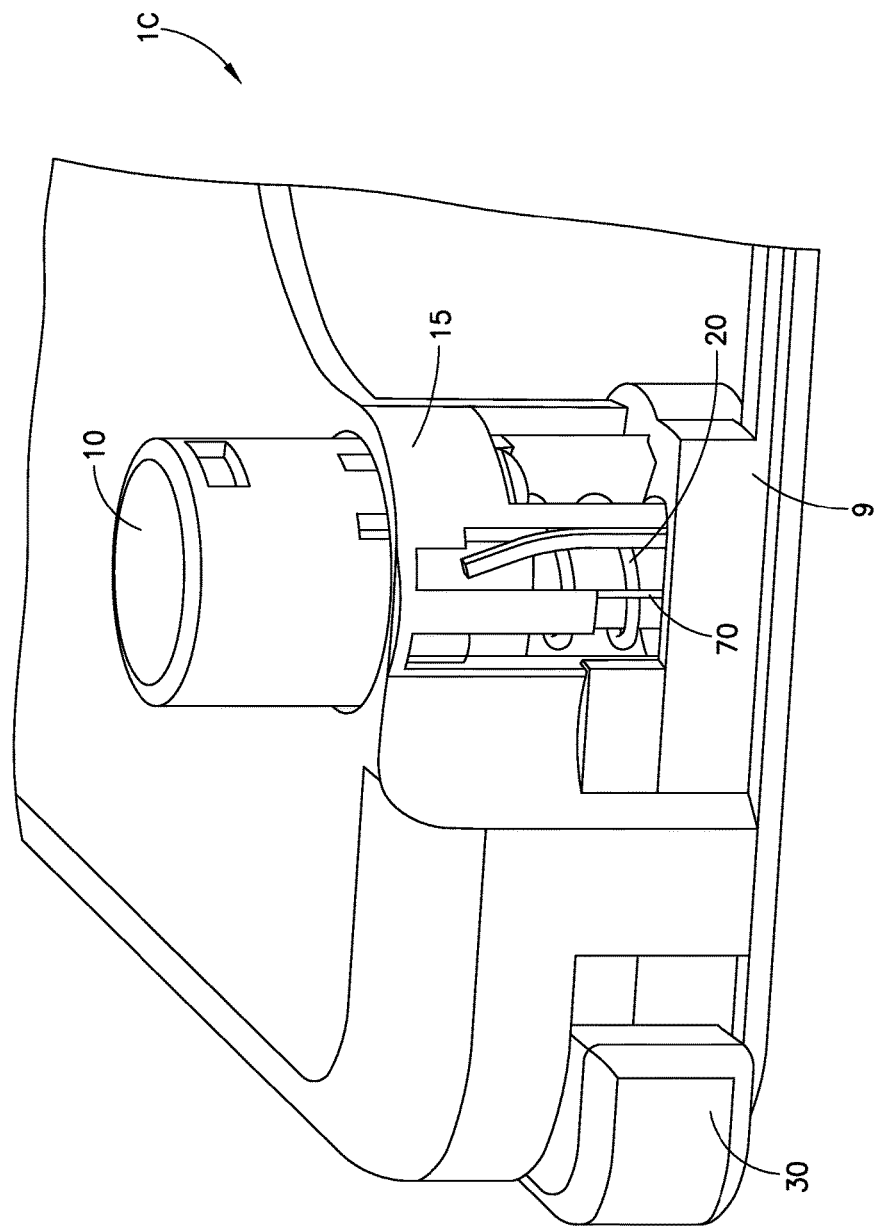
FIG. 12 is an enlarged partial cross-sectional view of the exemplary infusion device of FIG. 10A before activation in accordance with an embodiment of the present invention.

FIG. 12 illustrates a cutaway view of the device 1C with a portion of the cover of the device 1C removed for clarity. By pressing downward on the activation button 10, the cannula guide 15 is driven downward, inserting the cannula 70, into the infusion site. During this process, a spring 20 is compressed and exerts an upward force onto the cannula guide 15.

FIG. 13 illustrates the device 1C once the activation button 10 has been pressed fully downwards. The device 1C will remain in this position for the duration of infusion treatment. At the end of infusion treatment, by pressing on the retraction button 30, illustrated on a corner of the device, the activation button 10 will be rotated by a linkage 33 of the retraction button 30, around the cannula guide 15, which releases it from the base 9, allowing the spring 20 to de-compress and retract the cannula 70. The combination of elements above including the activation button 10 and spring 20 can be described as a cannula insertion device.

Figure 14A:
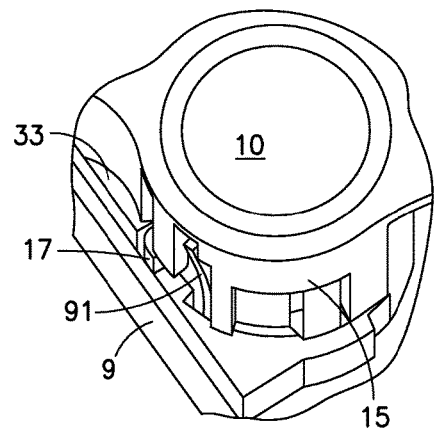
FIGS. 14A, 14B and 14C are partial cutaway views illustrating how the activation button s released from the base to retract the cannula.
Figure 14B:
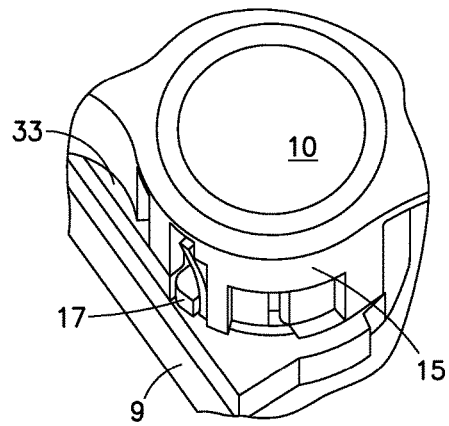
Figure 14C:
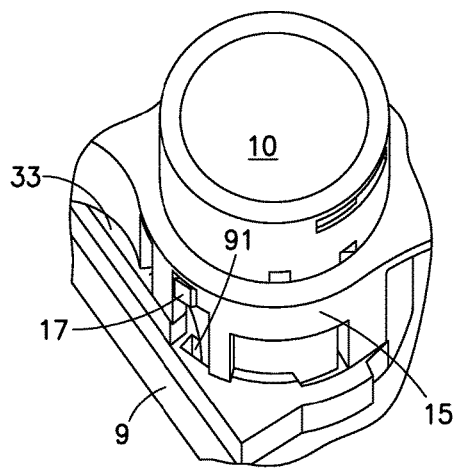

FIGS. 14A, 14B and 14C are partial cutaway views illustrating how the activation button 10 is released from the base 9 to retract the cannula 70. A locking tab 17 on the activation button 10 prevents the activation button 10 from being forced upward until the activation button 10 is rotated by the release button 30, as illustrated in FIG. 14A. FIG. 14B illustrates how, when the activation button 10 is rotated by the linkage 33, connected to the release button 30, as the release button 30 is partially pressed, around the cannula guide 15, the locking tab 17 is disconnected from the base 9 and can be forced upward by the spring 20. When the release button 30 is fully pressed, the activation button 10 moves upward, and the locking tab 17 deflects a flexible spoke 91 on the base 9. Once fully retracted the spoke 91 flexes back to its original position, underneath the locking tab 17, locking the activation button 10 in the retracted position. The combination of elements above that can include release button 30, linkage 33, locking tab 17 and spring 20 can be described as a cannula retraction device.

Figure 15:
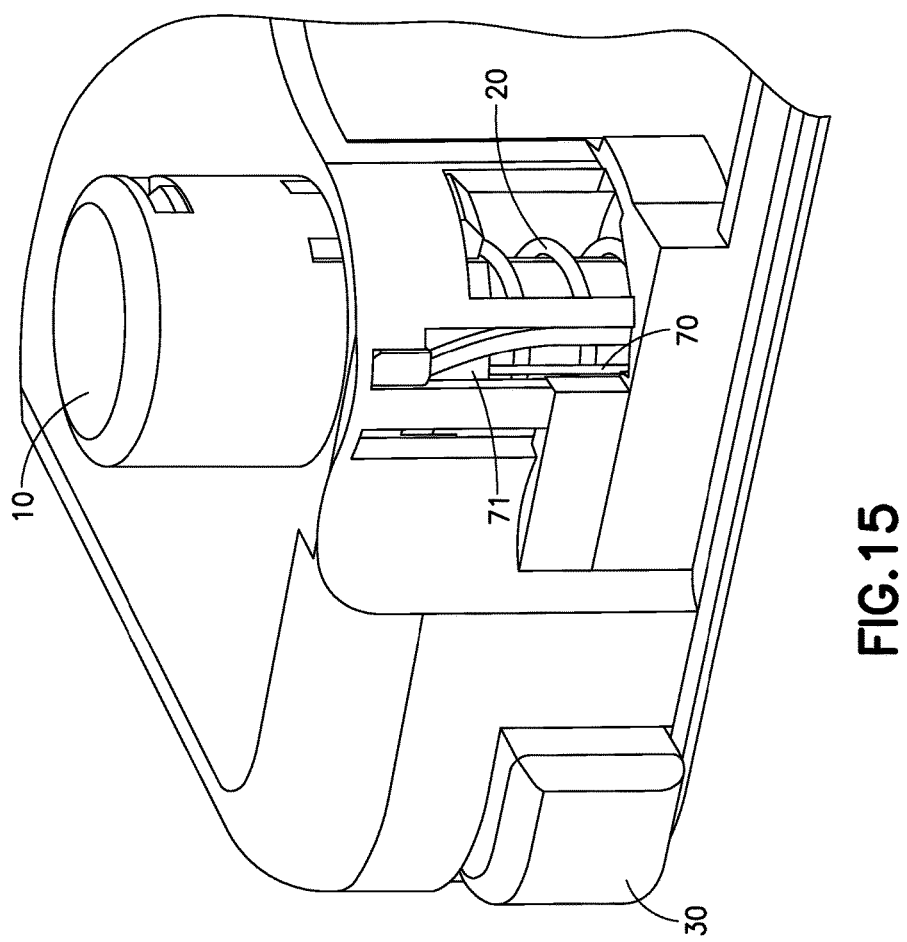
FIG. 15 is an enlarged partial cross-sectional view of the exemplary infusion device of FIG. 10A at the completion of activation in accordance with an embodiment of the present invention.

FIG. 15 illustrates the device 1C with the cannula 70 fully retracted inside the device 1C. The spring 70 has decompressed, forcing the cannula carrier 71 upward and removing the cannula 70 attached to the cannula carrier 71 from the infusion site. Since the locking tab 17 is trapped by the spoke 91, as illustrated in FIG. 14C, the device 1C cannot be activated a second time.

FIGS. 16-21 illustrate another embodiment of the invention in the form of an infusion device 1D with a rotating cannula hub insertion and retraction mechanism. Pressing downwardly on the activation button 10 drives a cannula carrier 71 downward, compresses a spring 20, and inserts the hollow metal cannula 70 into the infusion site. By pressing a separate retraction button 30, the cannula carrier 71 rotates and is no longer held downward by the activation button 10. The spring decompresses, forcing the cannula carrier 71 upward and removing the cannula 70 from the infusion site.

This device 1D is used to insert a cannula 70 into an infusion site, as well as to retract the cannula 70 from the infusion site. The actuation for the device 1D is derived from pushing downward on the activation button 10 by a user. The activation button 10 drives the cannula carrier 71 or cannula hub downward, which inserts the cannula 70 into the infusion site. At the same time, the activation button 10 also compresses a spring 20 that will later be used for the retraction of the cannula 70. When the retraction button 30 is pressed from a side of the device 1D in order to rotate the cannula carrier 71 slightly, which disengages it from the activation button 10 and allows the spring 20 to expand or decompress, the cannula carrier 71 is forced upward to remove the cannula 70 from the infusion site.

Figure 16A:
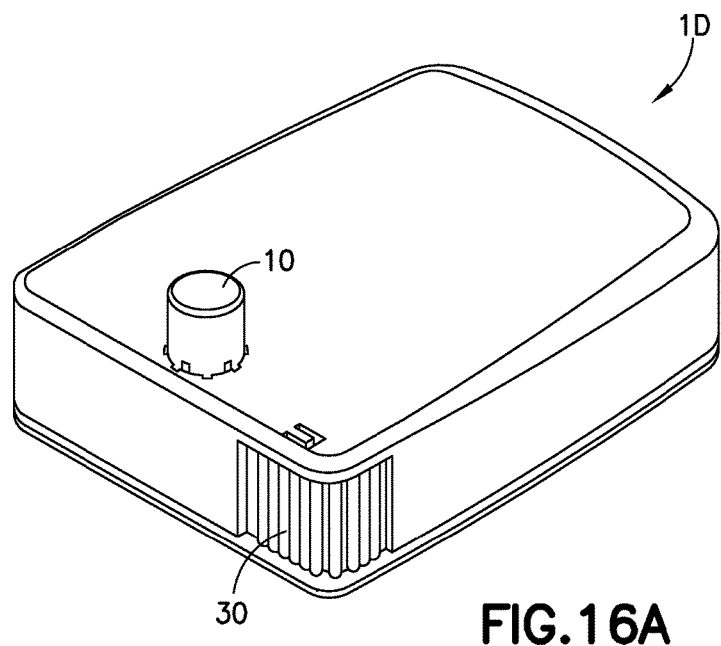
FIG. 16A is a perspective view of another exemplary infusion device prior to activation in accordance with an embodiment of the present invention.
Figure 16B:
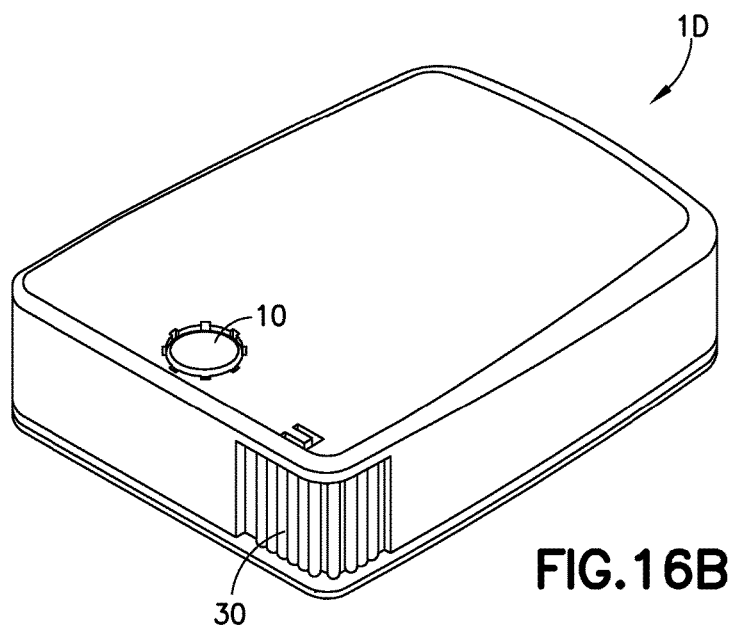
FIG. 16B is a perspective view of the exemplary infusion device of FIG. 16A after activation in accordance with an embodiment of the present invention.

FIG. 16A is a perspective view of the infusion device 1D prior to activation in accordance with an embodiment of the present invention. The device 1D is activated by pressing downward on the activation button 10, which protrudes from the top of the housing of the device 1D. FIG. 16B is a perspective view of the exemplary infusion device of FIG. 16A after activation.

Figure 17:
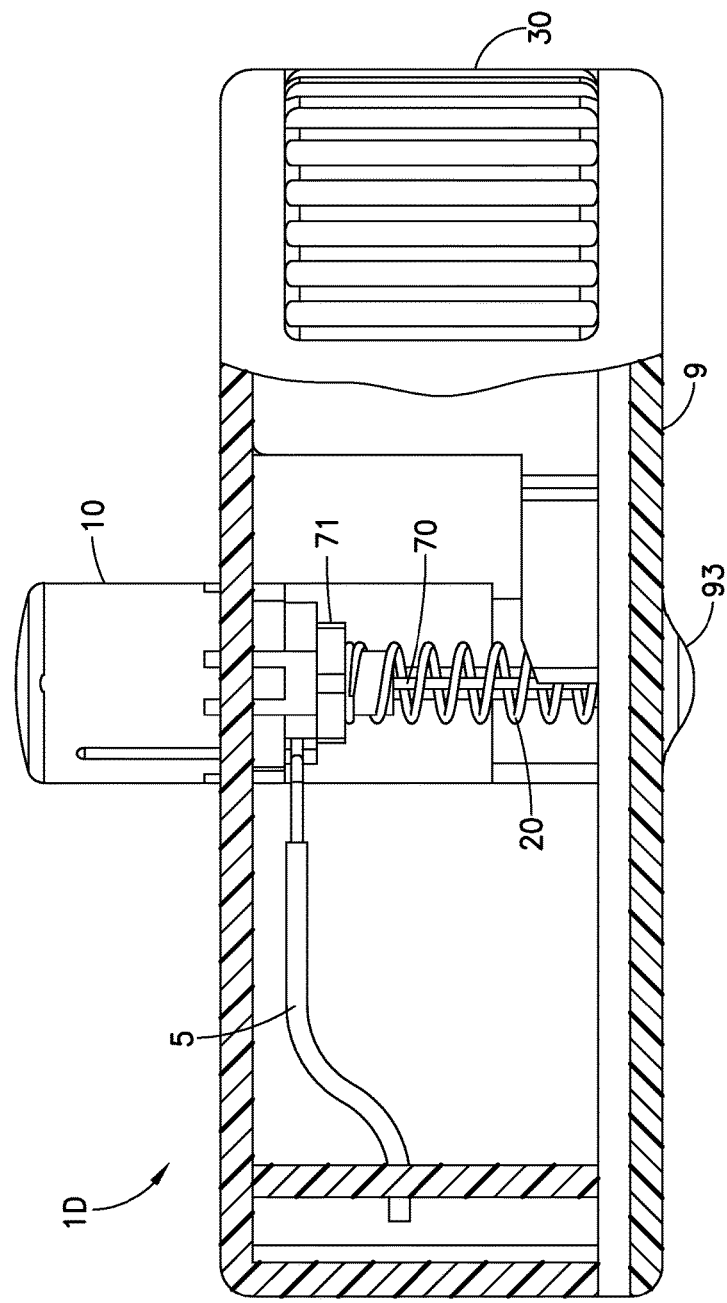
FIG. 17 is a cross-sectional view of the exemplary infusion device of FIG. 16A before activation in accordance with an embodiment of the present invention.

FIG. 17 is a cross-sectional view of the exemplary infusion device of FIG. 16A before activation in accordance with an embodiment of the present invention. FIG. 17 illustrates a cutaway view of the device 1D with a portion of the outer cover of the device 1D removed for clarity. By pressing downward on the activation button 10, the cannula carrier 71 or cannula hub is driven downward, inserting the cannula 70 into the infusion site. During this process, a spring 20 is compressed and exerts an upward force on the cannula carrier 71.

FIG. 18 is a cross-sectional view of the exemplary infusion device of FIG. 16A at the beginning of activation in accordance with an embodiment of the present invention. FIG. 18 illustrates the device 1D once the activation button 10 has been fully pressed downward. The device 1D will remain in this state for the duration of infusion therapy. The cannula 70 exits from a base 9 of the device 1D via a rounded bump 93 on the base 9, which stretches the skin to which the device 1D is attached to, enabling a clean insertion of the cannula 70 into the user's skin.

Figure 19B:
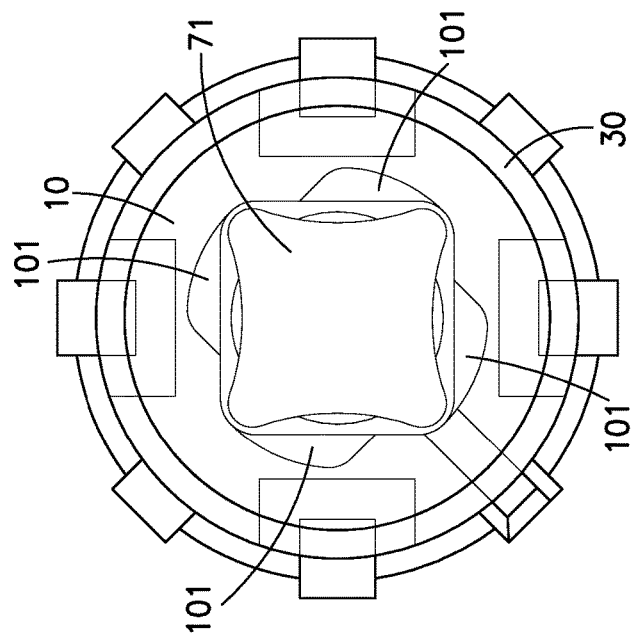
FIGS. 19A and 19B are top views of the exemplary infusion device of FIG. 16A illustrating the rotation of the cannula carrier in accordance with an embodiment of the present invention.
Figure 19A:
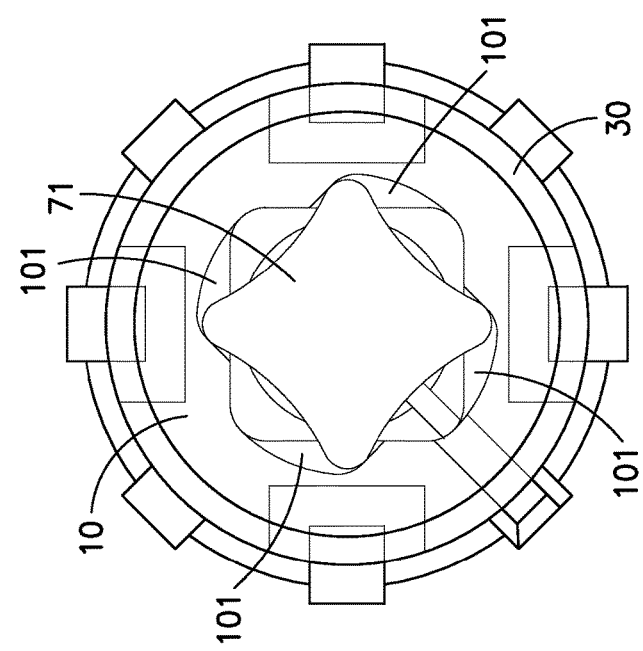

By pressing on the retraction button 30, preferably on a corner of the device, the cannula carrier 71 will be rotated, which releases the cannula carrier 71 from recesses or grooves 101 in the activation button 10, allowing the spring 20 to expand by decompressing and retract the cannula 70 from the infusion site, as illustrated in FIGS. 19A and 19B. FIGS. 19A and 19B are top views illustrating how the rotation of the cannula carrier 71 occurs in accordance with an embodiment of the present invention. FIG. 19A shows a top view of how the cannula carrier 71 is held in the activation button 10 prior to retraction. The shape of the cannula carrier 71 and the activation button 10 prevent the cannula carrier 71 from being forced upward when the cannula 70 is inserted into the infusion site, as corners of the cannula carrier 71 are locked into recesses or grooves 101, as illustrated in FIG. 19A. In other words, a portion of the cannula carrier 71 is locked onto the activation button 10 prior to the retraction of the cannula 70, as illustrated in FIG. 19A. FIG. 19B illustrates how, when the cannula carrier 71 is rotated by a linkage (not shown) connected to the retraction button 30 when the retraction button 30 is pushed, the corners of the cannula carrier are released from the recesses or grooves 101 in the activation button 10, and the cannula carrier 71 fits flush inside the activation button 10, freeing the cannula carrier 71 from being locked with the button 10, such that the cannula carrier can then be forced upward by the expansion or decompression of the spring 20. The combination of elements including cannula 10, spring 20, cannula carrier 71 can be used to describe a cannula insertion device, and the combination of elements including retraction button 30, cannula 10, spring 20 and cannula carrier 71 can be used to describe a cannula retraction device.

Figure 20:
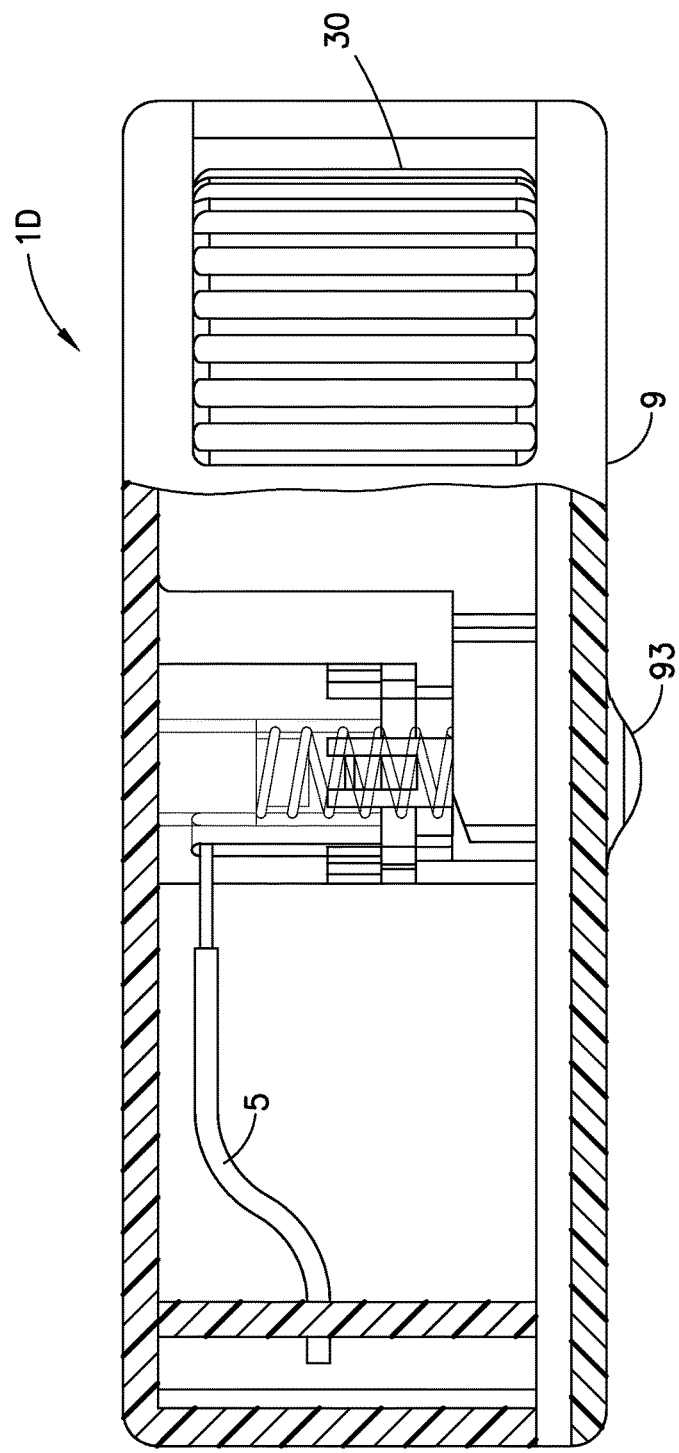
FIG. 20 is an enlarged partial cross-sectional view of the exemplary infusion device of FIG. 16A at the completion of activation in accordance with an embodiment of the present invention.

FIG. 20 is an enlarged partial cross-sectional view of the exemplary infusion device of FIG. 16A at the completion of activation in accordance with an embodiment of the present invention. FIG. 20 illustrates the device 1D with the cannula 70 fully retracted. It is noted that the activation button 10 also remains inside the device 1D. The spring 20 has expanded or decompressed, forcing the cannula carrier 71 upward and removing the cannula 70 from the infusion site. Since the activation button 10 does not return to its pre-activation position, it is not possible to activate the device 1D a second time.

FIGS. 21-27 illustrate another embodiment of the invention in the form of an infusion device 1E with a steel needle insertion and retraction mechanism having a manual push button or activation button 10 to insert a hollow indwelling cannula 70, preferably made or steel, into an infusion site, a user's skin. As the activation button 10 is pressed, a retraction spring 20 is loaded or compressed. The activation button 10 locks in the downward or pressed position until the user is ready to remove the cannula 70 from the infusion site. Before the device 1E is detached from a user, a retraction button 30, preferably on a side of the device 1E is pressed which retracts the cannula 70 by releasing the compressed spring 20 and permanently locks the cannula 70 inside of the housing of the device 1E to prevent a needle stick injury from being caused by the cannula 70 after the infusion therapy.

Figure 21:
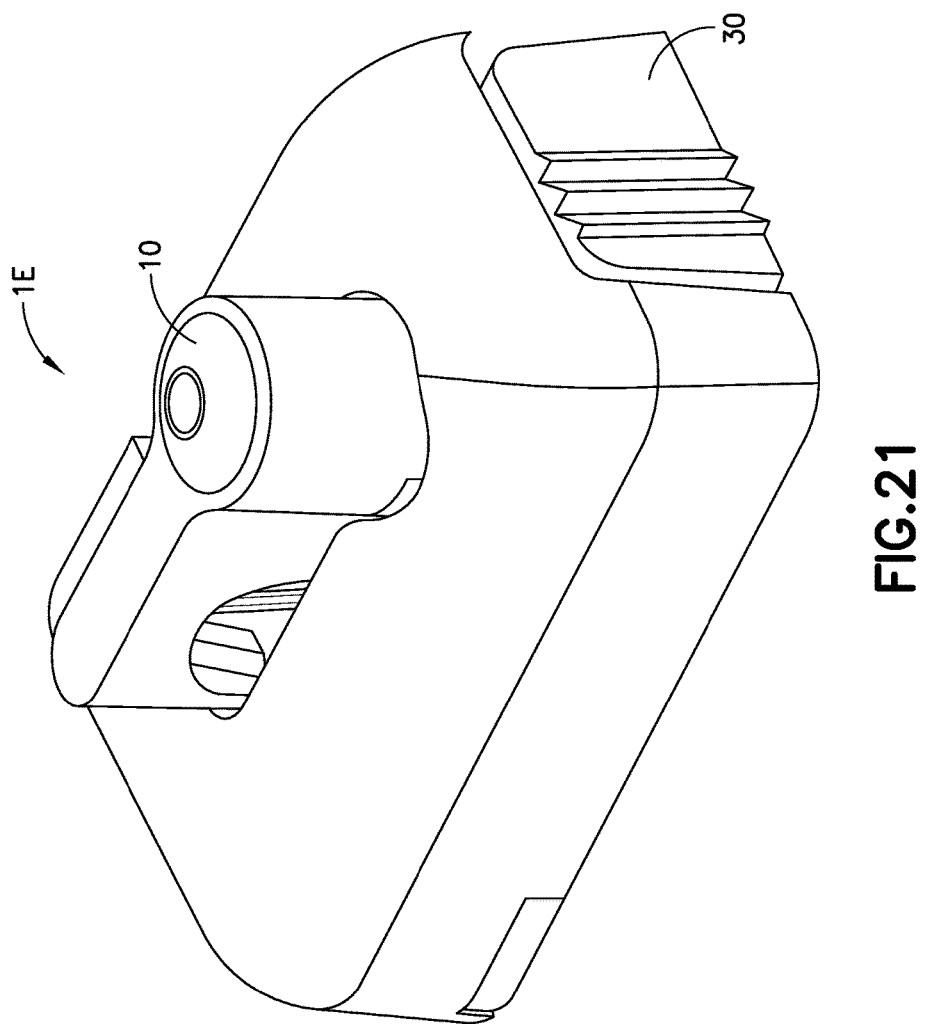
FIG. 21 is a perspective view of another exemplary infusion device prior to activation in accordance with an embodiment of the present invention.

FIG. 21 is a perspective view of an exemplary infusion device 1E illustrated prior to activation, prior to insertion of the cannula 70 in to an infusion site.

Figure 22:
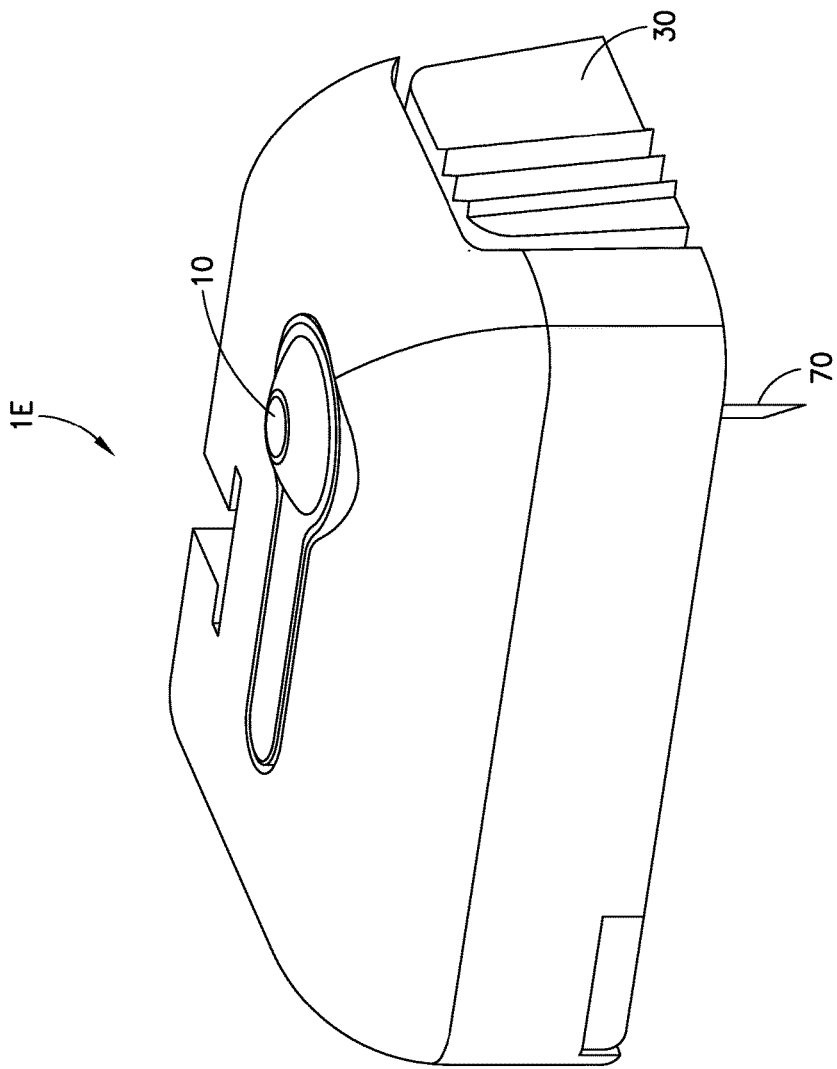
FIG. 22 is a perspective view of the exemplary infusion device of FIG. 21 after activation in accordance with an embodiment of the present invention.

FIG. 22 is a perspective view of the exemplary infusion device 1E of FIG. 21 after activation in accordance with an embodiment of the present invention. FIG. 22 illustrates the cannula 70 extending out of the device 1E and in position for infusion therapy.

Figure 23:
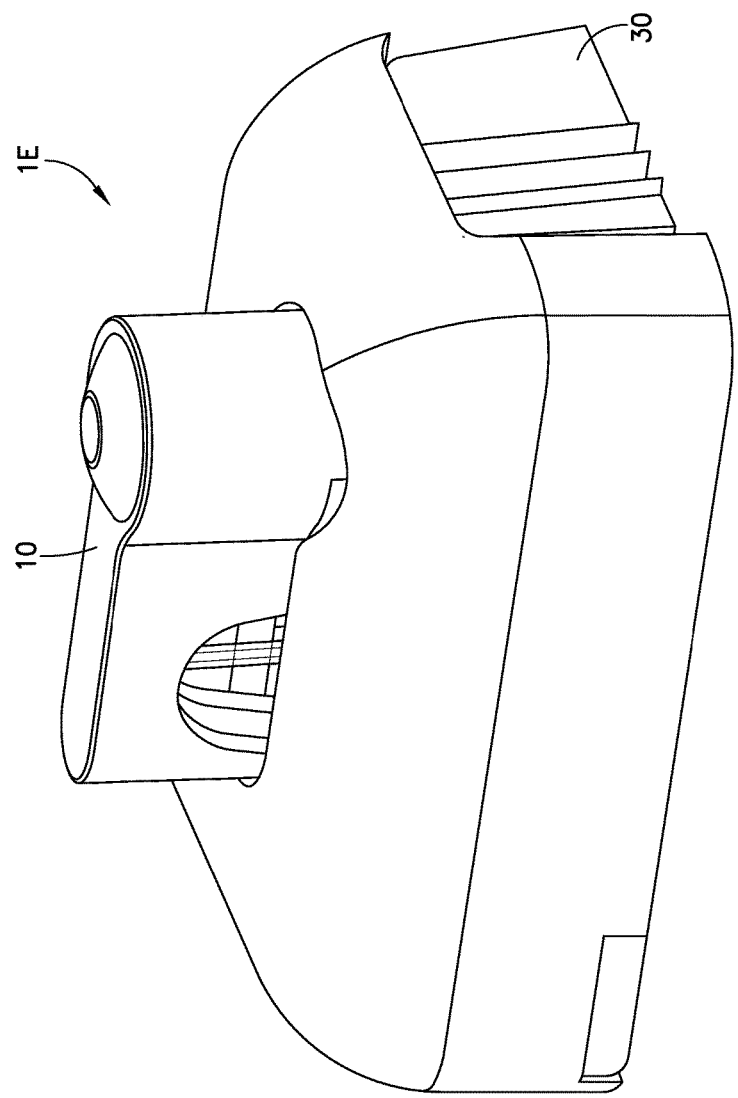
FIG. 23 is a perspective view of the exemplary infusion device of FIG. 21 after the retraction of the cannula in accordance with an embodiment of the present invention.

FIG. 23 is a perspective view of the exemplary infusion device 1E after retraction of the cannula 70 in accordance with an embodiment of the present invention. FIG. 23 illustrates the device 1E after the user has pushed the needle retraction button 30, prior to the device 1E being removed from a user.

Figure 24:
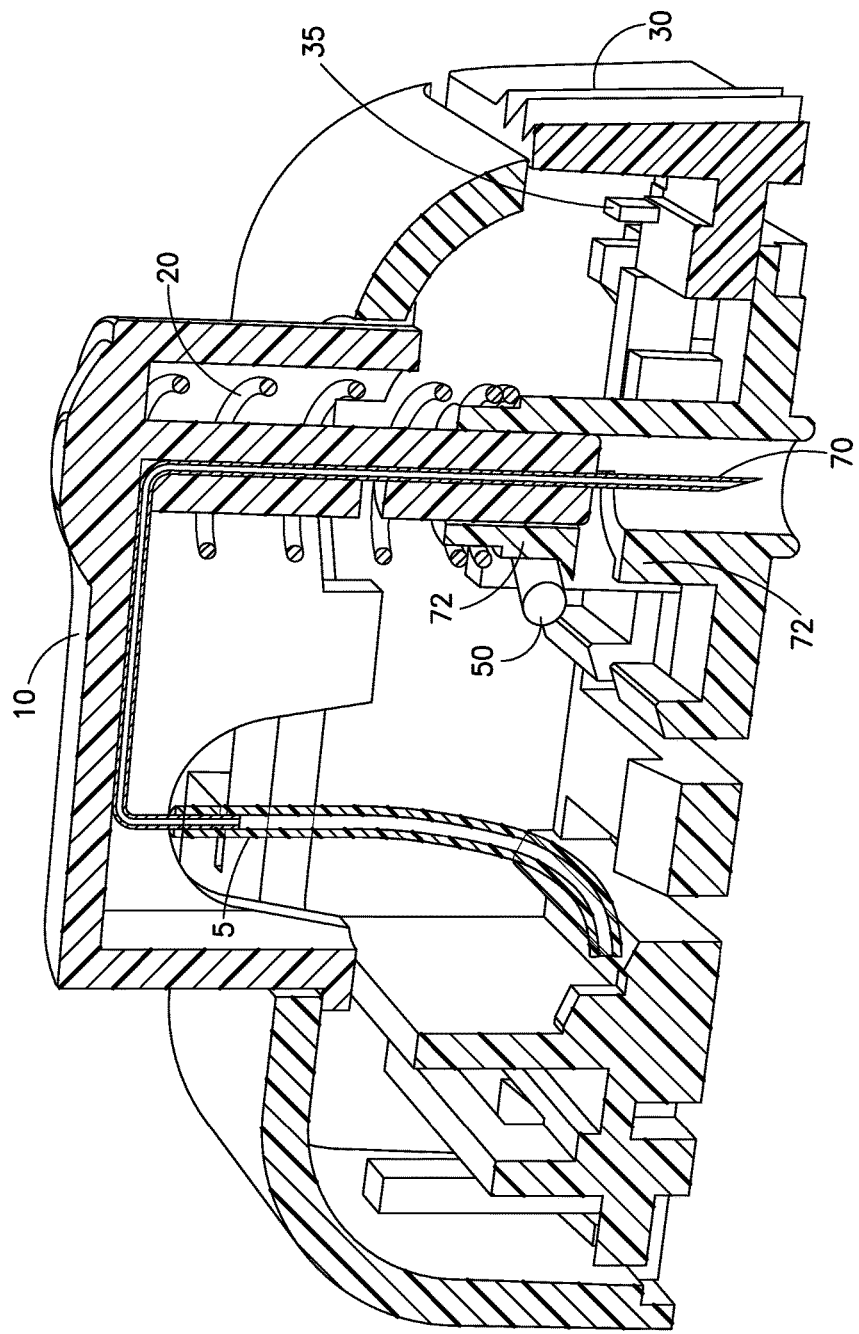
FIG. 24 is a cross-sectional view of the exemplary infusion device of FIG. 21 before activation in accordance with an embodiment of the present invention.

FIG. 24 is a cross-sectional view of the exemplary infusion device 1E of FIG. 21 before activation in accordance with an embodiment of the present invention. The activation button 10 can be used as pathway for the cannula 70 formed in an "L" or "U" shape. The flexible tubing 5 connected to a pump/reservoir (not shown) will connect to an end of the steel cannula 70 to transfer infusate to the infusion site. The activation button 10 is illustrated as being elongated along a length of the infusion device 1E for easier activation by a user.

Figure 25:
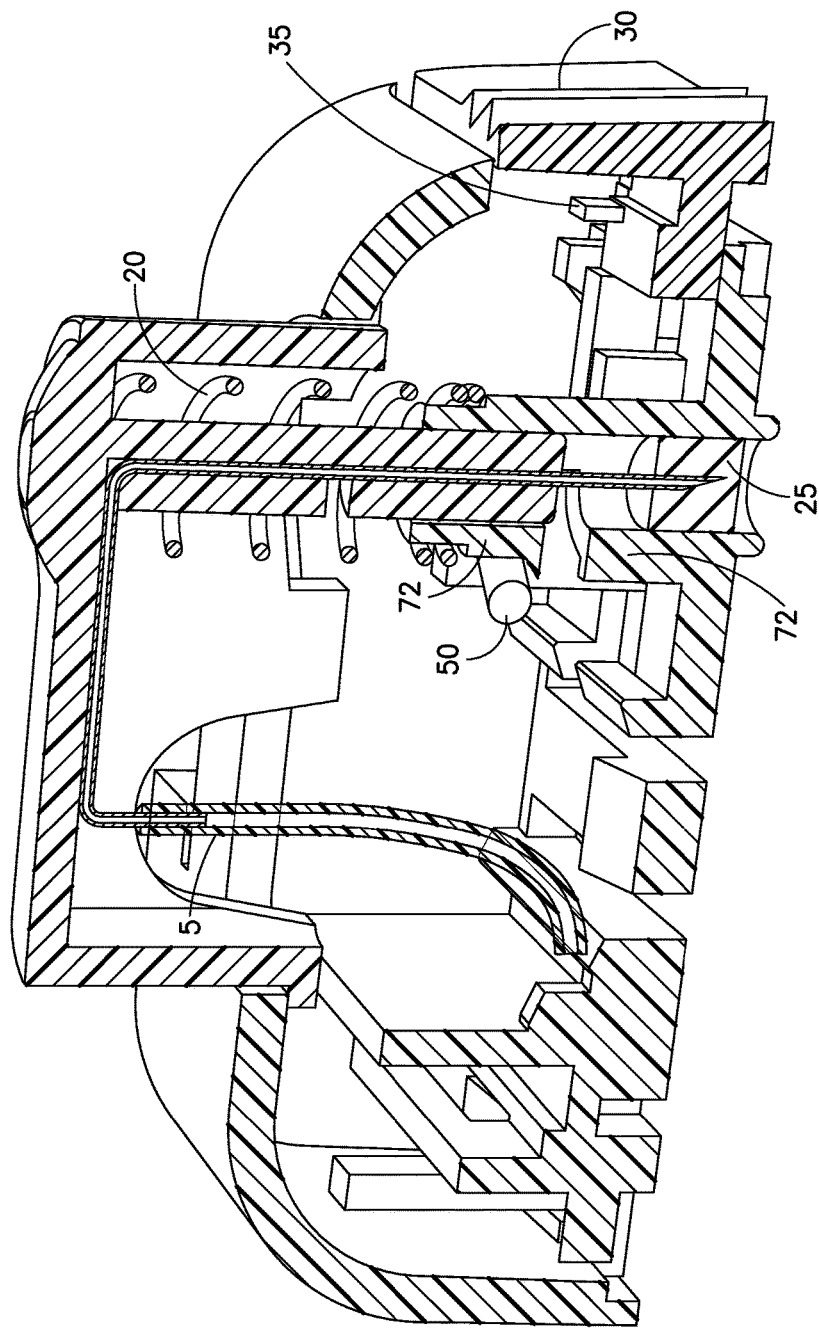
FIG. 25 is a cross-sectional view of the exemplary infusion device of FIG. 21 before activation in accordance with an embodiment of the present invention.

FIG. 25 is a cross-sectional view of the exemplary infusion device 1E before activation in accordance with an embodiment of the present invention. No cannula exit is necessary since the insertion mechanism is out of the water-tight seal. However, if a piston style pump is used and the fluid path 5 must be occluded to fill the device, the tip of the cannula 70 could be embedded in a septum 25 in the pre-activation configuration as indicated.

Figure 26:
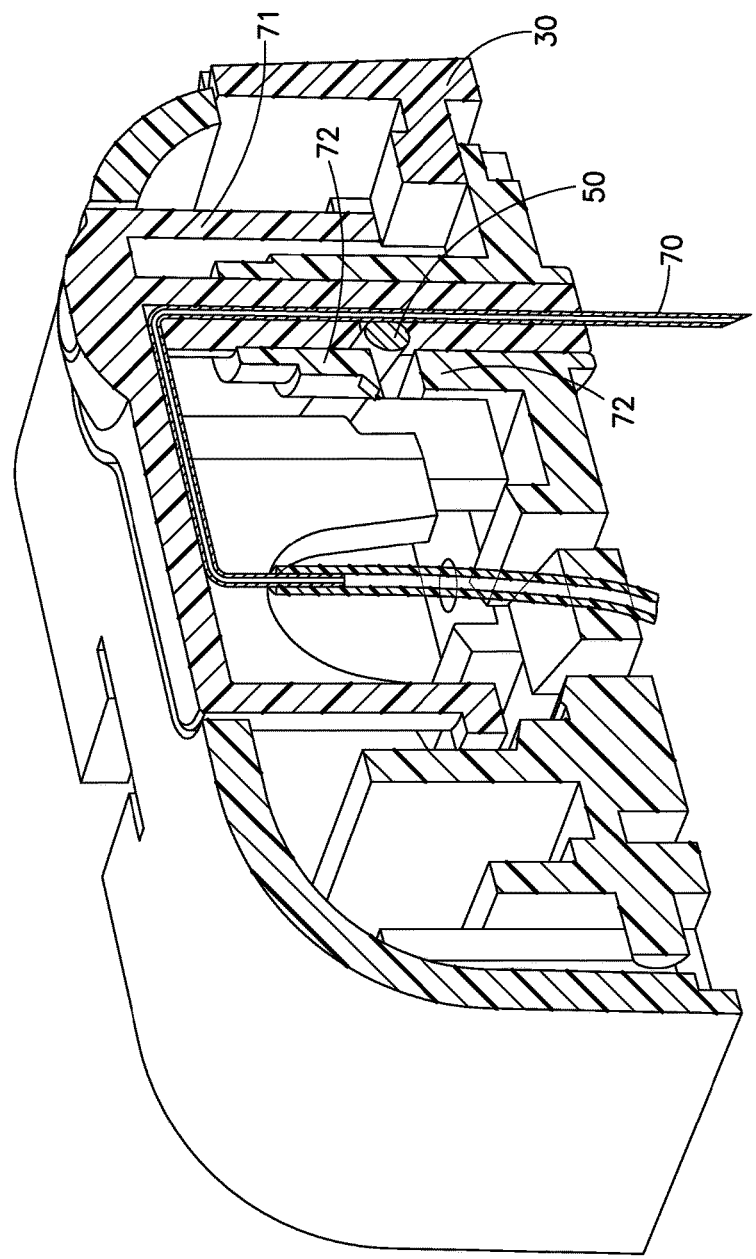
FIG. 26 is a cross-sectional view of the exemplary infusion device of FIG. 21 during infusate therapy in accordance with an embodiment of the present invention.

FIG. 26 is a cross-sectional view of the exemplary infusion device 1E during infusate therapy in accordance with an embodiment of the present invention. After the device 1E is filled with infusate (not shown) and applied to the patient's skin, typically by adhesive, the activation button 10 is pressed downward, inserting the steel cannula 70 into the infusion site or user's skin. The needle hub or cannula carrier 71 overdrives slightly to overcome tenting of the skin of the user. As the activation button 10 is pressed downward, a flexible beam 50 on the retraction button 30 is pressed over a retention device 72 in the base barrel or cannula carrier 71 into a slot which retains the insertion button 10 in the down position. The retraction spring 20 is compressed in this configuration.

Figure 27:
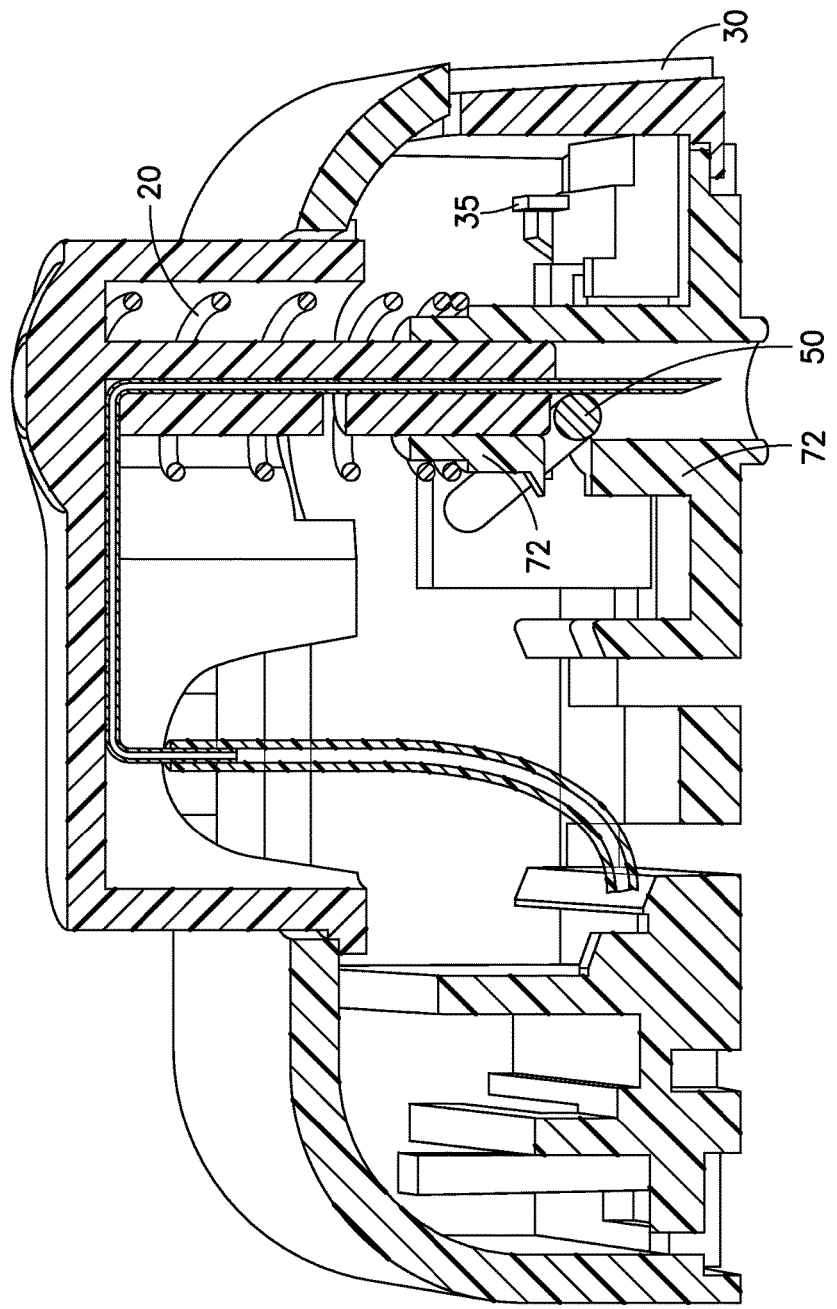
FIG. 27 is a cross-sectional view of the exemplary infusion device of FIG. 21 at the completion of deactivation in accordance with an embodiment of the present invention.

FIG. 27 is a cross-sectional view of the exemplary infusion device 1E at the completion of deactivation in accordance with an embodiment of the present invention. When the user is ready to remove the device, the retraction button 30 on the side of the device 1E is pressed. The breakable ribs 35 break allowing the retraction button 30 to be pressed inward, which moves the beam 50 out of its slot on the retention device 72, thereby allowing the spring 20 to push the activation button 10 upward. When the retraction button 30 is released, a molded spring which can be molded into the retraction button 30 pushes the beam 30 into the slot of the retention device 72, which permanently locks the activation button 10 in the retracted position and the tip of the cannula 70 inside of the housing of the device 1E. For complete removal of the device 1E, the adhesive patch (not shown) on a base of the device 1E would then be peeled back to remove the device 1E.

The combination of elements above, including one or more of activation button 10, spring 20, beam 50, retention device 72 can be described as a cannula insertion device, and the combination including one or more of retraction button 30, breakable ribs 35, activation button 10, spring 20, beam 50, retention device 72 can be described as a cannula retraction device.

Figure 28:
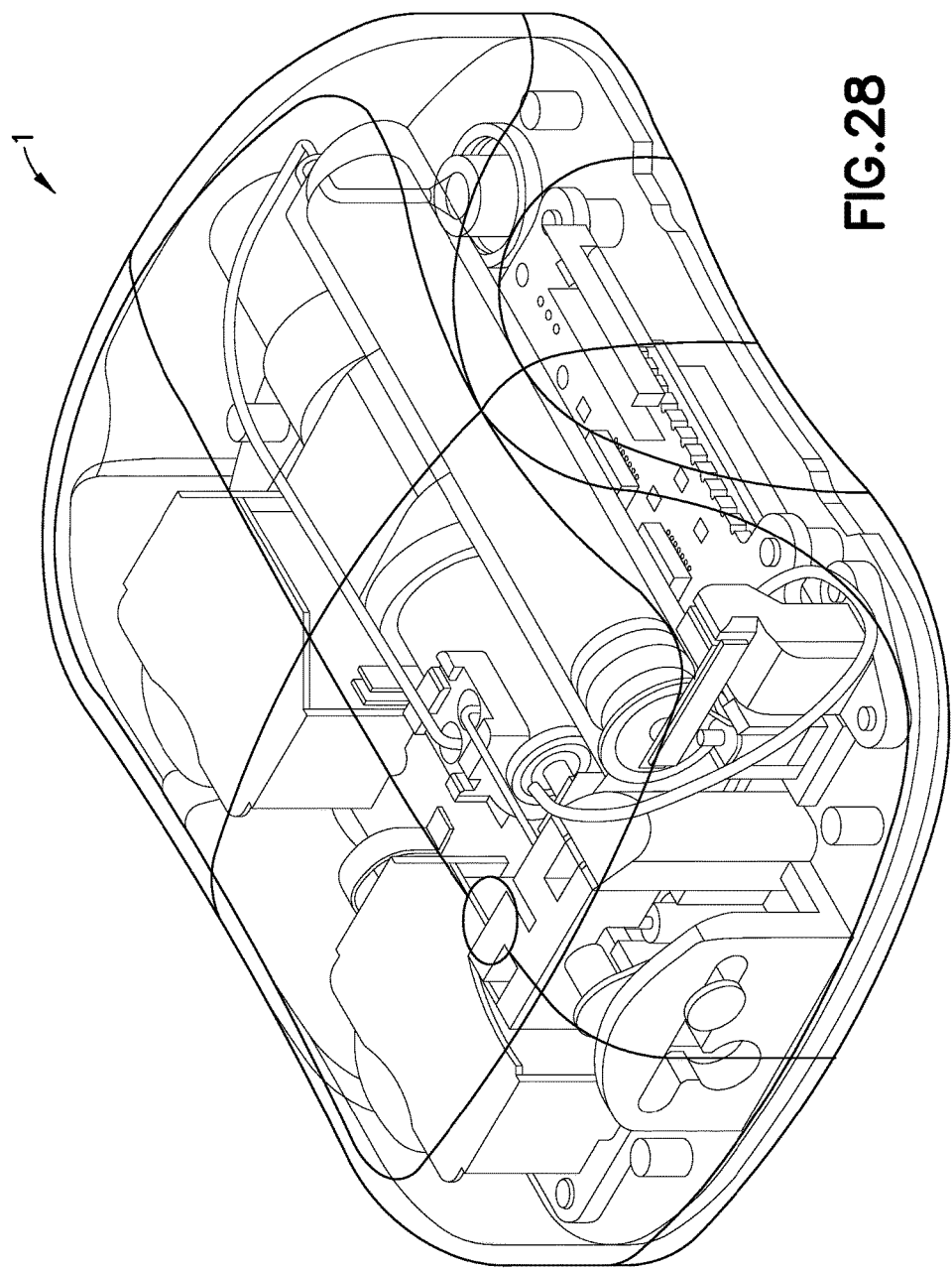
FIG. 28 is a perspective view of a patch pump incorporating a low-profile cannula insertion device, illustrated without a cover for clarity.
Figure 29:
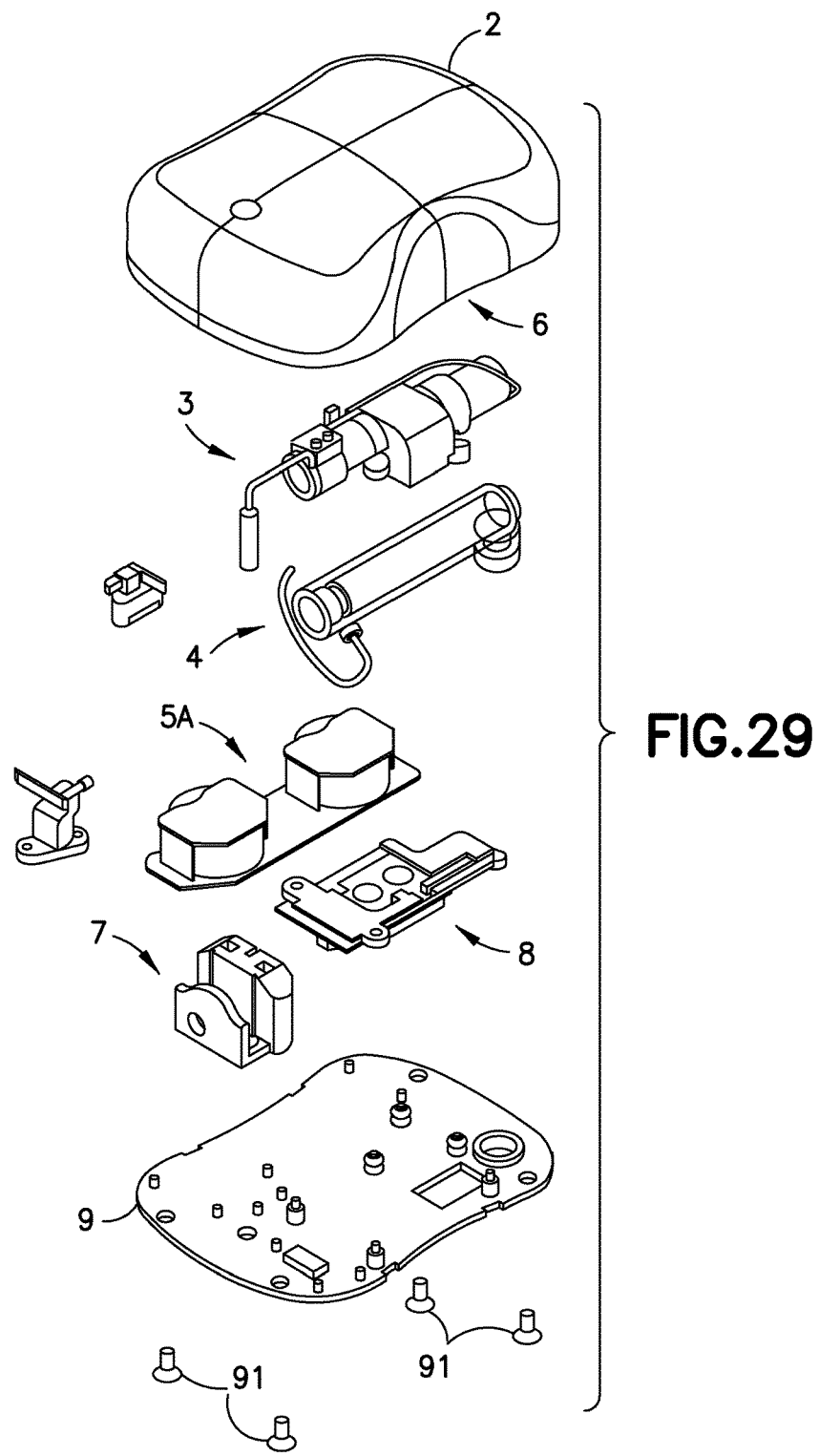
FIG. 29 is an exploded view of the various components of the patch pump of FIG. 1, illustrated with a cover.

FIG. 28 is a perspective view of another exemplary embodiment of a patch pump 1 according to an exemplary embodiment of the invention. The patch pump 1 is illustrated with a see-through cover for clarity and illustrates various components that are assembled to form the patch pump 1. FIG. 29 is an exploded view of the various components of the patch pump of FIG. 1, illustrated with a solid cover 2. The various components of the patch pump 1 may include: a reservoir 4 for storing insulin; a pump 3 for pumping insulin out of the reservoir 4; a power source 5A in the form of one or more batteries; an insertion mechanism 7 for inserting an inserter needle with a catheter into a user's skin; control electronics 8 in the form of a circuit board with optional communications capabilities to outside devices such as a remote controller and computer, including a smart phone; a dose button 6 on the cover 2 for actuating an insulin dose, including a bolus dose; and a base 9 to which various components above may be attached via fasteners 910. The patch pump 1 also includes various fluid connector lines that transfer insulin pumped out of the reservoir 4 to the infusion site.

It should be understood that inserter mechanisms come in various configurations. In some embodiments, the inserter mechanism inserts a soft catheter into the skin. In these embodiments, typically the soft catheter is supported on a rigid insertion needle. The insertion needle is inserted into the skin along with the soft catheter, and then retracted from the skin, leaving the soft catheter in the skin. In other embodiments, a soft catheter is not provided, and the insertion needle remains in the skin and forms a portion of the insulin flow path to deliver insulin until the infusion is finished. Insertion needles are typically hollow, and need to be hollow if they form part of the insulin flow path. However, insertion needles that support a soft catheter and then retract may be solid or hollow. If the insertion needle deploys a soft catheter, and retracts but remains part of the insulin flow path, then the insertion needle should be hollow. However, if the insertion needle deploys a soft catheter and then retracts but does not form part of the insulin flow path, then the insertion needle may be solid or hollow. In either case, the insertion needle is preferably rigid enough to reliably penetrate the skin, but otherwise may be made flexible enough to provide comfort to the user.

Figure 30:
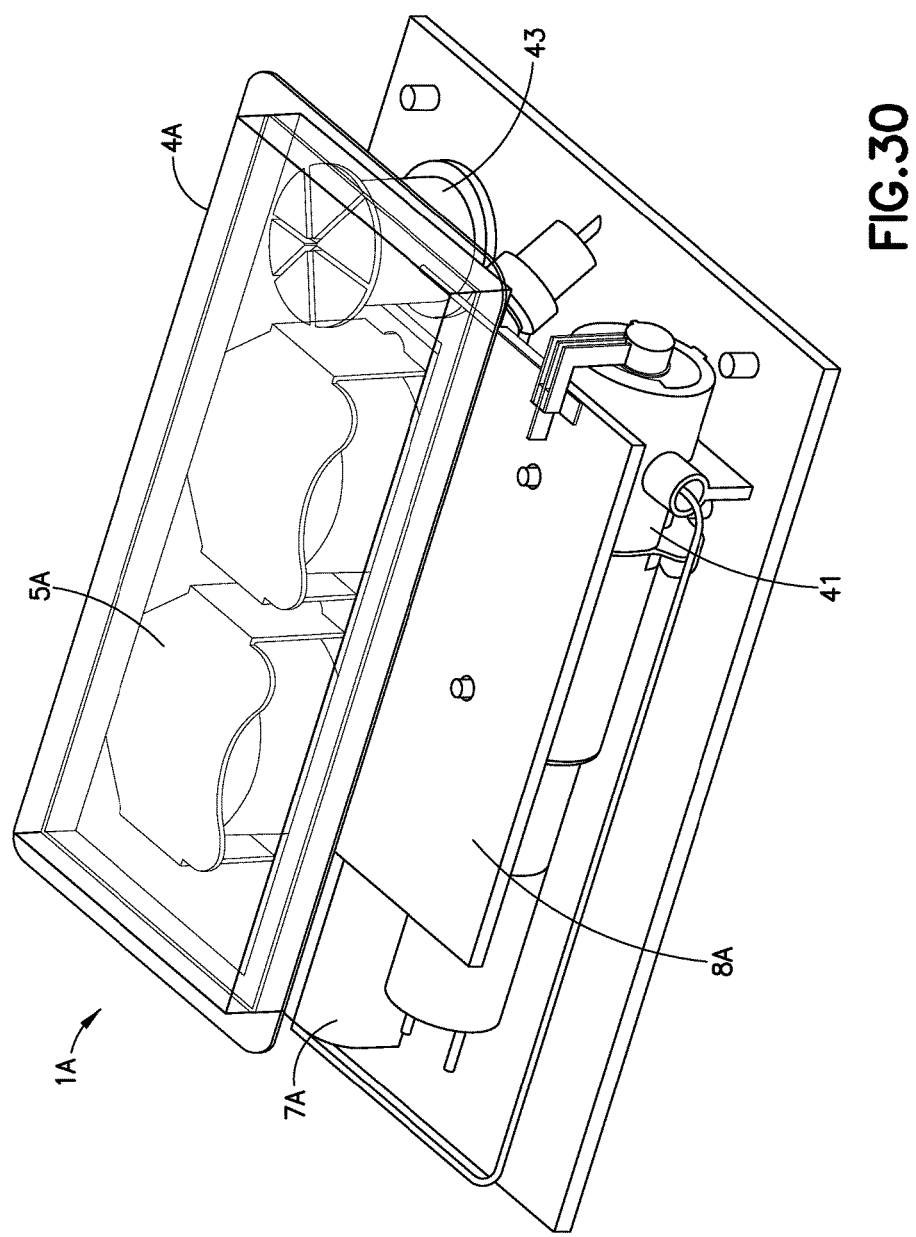
FIG. 30 is a perspective view of an alternative design for a patch pump having a flexible reservoir, illustrated without a cover.

FIG. 30 is a perspective view of an alternative design for a patch pump 1AA having a flexible reservoir 4A, and illustrated without a cover. Such arrangement may further reduce the external dimensions of the patch pump 1A, with the flexible reservoir 4A filling voids within the patch pump 1A. The patch pump 1A is illustrated with a conventional cannula insertion device 7A that inserts the cannula, typically at an acute angle, less than 90 degrees, at the surface of a user's skin. The patch pump 1A further comprises: a power source 5A in the form of batteries; a metering sub-system 41 that monitors the volume of insulin and includes a low volume detecting ability; control electronics 8A for controlling the components of the device; and a reservoir fill port 43 for receiving a refill syringe 45 to fill the reservoir 4A.

FIG. 31 is a patch-pump fluidic architecture and metering sub-system diagram of the patch pump 1AA of FIG. 30. The power storage sub-system for the patch pump 1AA includes batteries 5A. The control electronics 8A of the patch pump 1AA may include a microcontroller 81, sensing electronics 82, pump and valve controller 83, sensing electronics 85, and deployment electronics 87, that control the actuation of the patch pump 1AA. The patch pump 1AA includes a fluidics sub-system that may include a reservoir 4A, volume sensor 48 for the reservoir 4A, a reservoir fill port 43 for receiving a refill syringe 45 to refill the reservoir 4A. The fluidics sub-system may include a metering system comprising a pump and valve actuator 411 and an integrated pump and valve mechanism 413. The fluidics sub-system may further include an occlusion sensor, a deploy actuator, as well as the cannula 47 for insertion into an infusion site on the user's skin. The architecture for the patch pumps of FIGS. 28 and 29 is the same or similar to that which is illustrated in FIG. 31.

Figure 32A:
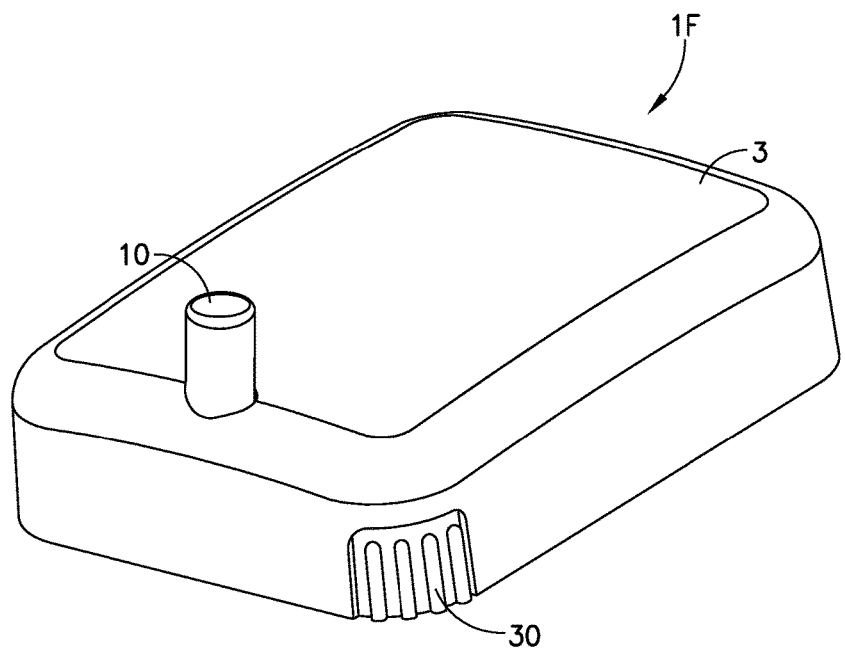
FIG. 32A is a perspective view of another exemplary infusion device prior to activation in accordance with an embodiment of the present invention.
Figure 32B:
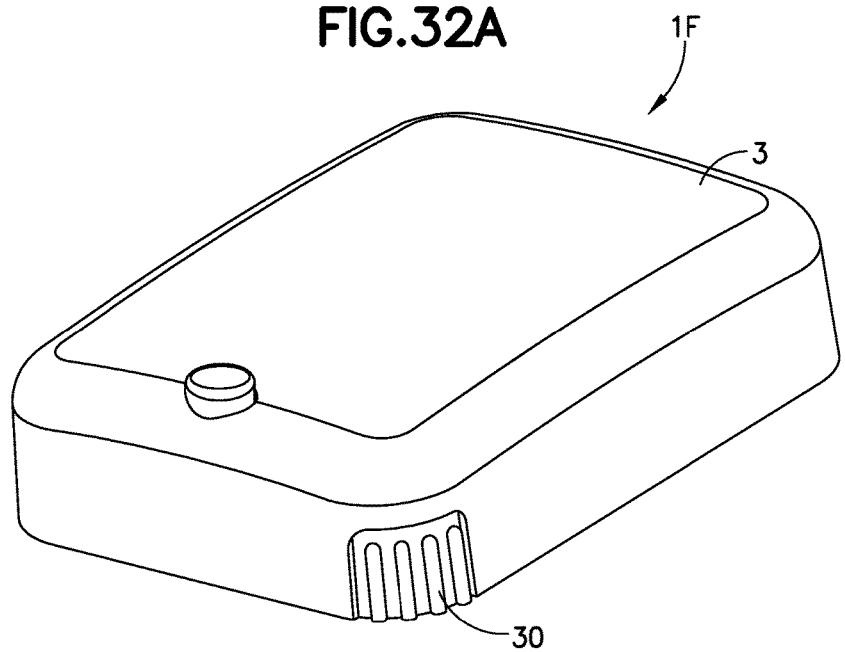
FIG. 32B is a perspective view of the exemplary infusion device of FIG. 32A after activation in accordance with an embodiment of the present invention.

FIG. 32A is a perspective view of another exemplary infusion device 1F, shown prior to activation. This embodiment has similarities with the embodiment of FIGS. 1A-5. FIG. 32B is a perspective view of the exemplary infusion device 1F of FIG. 32A after activation in accordance with an embodiment of the present invention.

Figure 33:
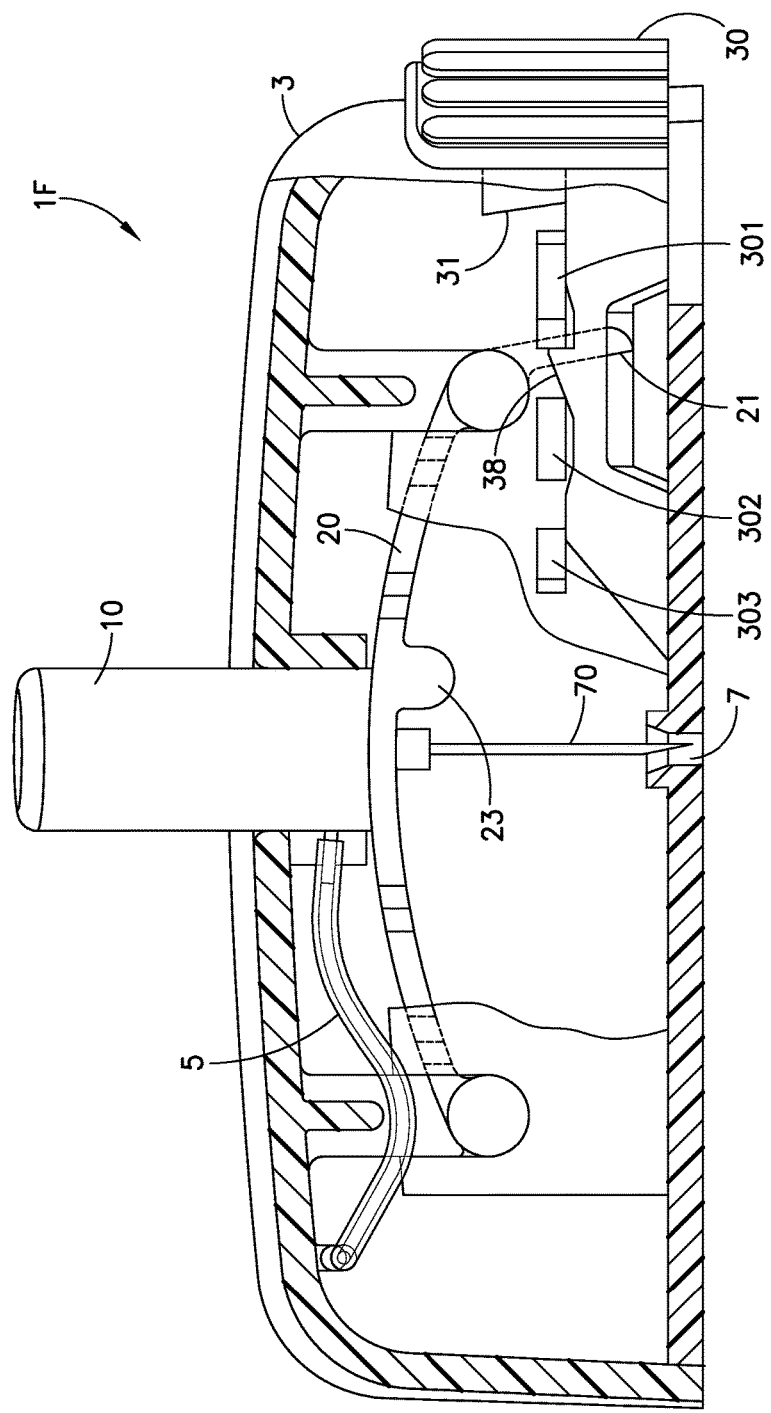
FIG. 33 is an enlarged cross-sectional view of another embodiment of the present invention.

FIG. 33 is an enlarged cross-sectional view of the infusion device 1F of FIG. 32A. The cutaway view illustrates the infusion device 1F prior to activation. In this embodiment, several modifications to the embodiment of FIGS. 1A-5 have been made in order to improve performance, manufacturability, and user comfort. The user presses directly downward on the activation button 10 until the bi-stable band 20 changes form and completely inserts the cannula 70 into the infusion site/user's skin. FIG. 33 illustrates a small arm 21 of the bi-stable band in a downward position.

FIG. 34 is an enlarged cross-sectional view of the exemplary infusion device of FIG. 32A after activation. The cutaway view of FIG. 34 illustrates the infusion device 1F with the cannula 70 extending out of the exit aperture 7 and the cannula 70 fully inserted into the infusion site. Once the activation button 10 has been pressed completely downward, as shown in FIG. 34, the bi-stable band 20 changes shape from that in FIG. 33 to that of FIG. 34. FIG. 33 illustrates the bi-stable band 20 with a convex upper surface and a concave lower surface, and FIG. 34 illustrates the bi-stable band 20 with a convex upper surface and a concave lower surface, with the small arm 21 of the band 20 pivoted in an upward direction from that of FIG. 33. Infusion therapy occurs in the position of FIG. 34 in which infusate delivered from the flexible tubing 5 flows into one end of the cannula 70 and out of the sharp end thereof into the infusion site.

The retraction button 30 extends further into the device than the embodiment of FIGS. 1A-5. An inclined ramp 31 extends from the retraction button 30, as illustrated in FIGS. 33 and 34. The lower surface of the bi-stable band 23 includes a bump 23, and when the activation button 10 is pushed fully downward, as illustrated in FIG. 34, the bump 23 abuts or is in close proximity to a ramp 39 of the retraction button 30. As illustrated in FIGS. 33 and 34, an auxiliary ramp 38 is held in position between the first and second tabs 301, 302.

In order to retract the cannula 70 from the infusion site, the retraction button 30 is pressed inward, as illustrated in FIG. 35, and the auxiliary ramp 38 is moved into a position which pushes the ramp 39 against the bump 23, causing the ramp 39 to press upward on the activation button 10. The pushing motion of the retraction button 30 lifts the activation button 10 high enough to cause the bi-stable band 20 to revert back to its original shape as in FIG. 33, causing the full retraction of the cannula 70 from the infusion site, as the activation button is pushed out of the device 1F, as in FIG. 33.

FIG. 35 is an enlarged cross-sectional view of the exemplary infusion device of FIG. 32A at the completion of retraction of the cannula 70. The cutaway view of the device illustrated in FIG. 35 illustrates the cannula 70 after it has been fully retracted from the infusion site into the infusion device 1F. FIG. 35 illustrates the infusion device 1F after the retraction button 30 has been fully pressed inward, causing the activation button 30 and cannula 70 to retract. In this position, the small arm 21 of the bi-stable band 20 is positioned next to a locking surface 37 of the retraction button 30. The retraction button 30 is pushed further to move the auxiliary ramp 38 to a position between the second and third tabs 302, 303 to prevent the reactivation of the device 1F, as illustrated in FIG. 35. In this position, the device 1F is locked, preventing a user from being able to press down on the activation button 10 and reinsert the cannula 70 a second time.

The combination of elements above, including one or more of 10, bi-stable band or spring 20, bump 23, activation button 30, tabs 301-303 can be described as a cannula insertion device, as well as a cannula retraction device.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of the appended claims and their equivalents.

The invention claimed is:

1. An infusion device, comprising:
   a body;
   a cannula housed in the body;
   a cannula insertion device activated by a first button acting on a first portion of a spring device to cause the spring device to drive the cannula to an inserted position;
   a cannula retraction device activated by a second button acting on a second portion of the spring device;
   wherein when the cannula insertion device is activated, the cannula extends at least partly out of the body and into an infusion site; and
   wherein when the cannula retraction device is activated after the cannula insertion device has been activated, the cannula retracts into the body.

2. The infusion device as claimed in claim 1, further comprising a fluid reservoir.

3. The infusion device as claimed in claim 2, wherein the cannula is a hollow hypodermic needle in communication with the fluid reservoir.

4. The infusion device as claimed in claim 3, wherein one end of the cannula is inserted into the infusion site on a user and another end of the cannula is in fluid communication with the fluid reservoir.

5. The infusion device as claimed in claim 2, wherein the fluid reservoir comprises insulin.

6. The infusion device as claimed in claim 1,
   wherein the spring device deforms when the cannula insertion device is activated.

7. The infusion device as claimed in claim 6, wherein the spring device comprises a bi-stable band.

8. The infusion device as claimed in claim 7, wherein the bi-stable band further comprises a bump for changing shape of the bi-stable band.

9. The infusion device as claimed in claim 6, further comprising a helical post configure to actuate the cannula insertion device and the cannula retraction device.

10. The infusion device as claimed in claim 1, wherein the spring device returns substantially to an original shape when the cannula retraction device is activated.

11. The infusion device as claimed in claim 1, wherein when the cannula insertion device is activated, the cannula is prevented from returning into the body.

12. The infusion device as claimed in claim 1, wherein when the cannula retraction device is activated, the cannula is permitted to return into the body.

13. The infusion device as claimed in claim 1, wherein one of the cannula insertion device and the cannula retraction device rotates upon activation.

14. A method for an infusion device, comprising the steps of:
   activating a cannula insertion device by pressing a first button that interacts with a first portion of a spring device to cause the spring device to drive a cannula at least partly out of a body of the infusion device while biasing the spring device; and
   activating a cannula retraction device by pressing a second button that interacts with a second portion of the spring device to release the spring device and retract the cannula into the body.

15. The method of claim 14, wherein the infusion device is configured to infuse insulin.

* * * * *